United States Patent
Landvik et al.

(10) Patent No.: US 9,102,928 B2
(45) Date of Patent: *Aug. 11, 2015

(54) POLYPEPTIDES HAVING GLUCOAMYLASE ACTIVITY AND POLYNUCLEOTIDES ENCODING SAME

(71) Applicants: NOVOZYMES A/S, Bagsvaerd (DK); NOVOZYMES NORTH AMERICA, INC., Franklinton, NC (US)

(72) Inventors: Sara Landvik, Vedbaek (DK); Marc Dominique Morant, Copenhagen (DK); Keiichi Ayabe, Chiba (JP); Guillermo Coward-Kelly, Wake Forest, NC (US)

(73) Assignees: NOVOZYMES A/S, Bagsvaerd (DK); NOVOZYMES NORTH AMERICA, INC. NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/916,042

(22) Filed: Jun. 12, 2013

(65) Prior Publication Data

US 2013/0267002 A1    Oct. 10, 2013

Related U.S. Application Data

(63) Continuation of application No. 13/500,325, filed as application No. PCT/US2010/058424 on Nov. 30, 2010, now Pat. No. 8,557,541.

(60) Provisional application No. 61/265,526, filed on Dec. 1, 2009, provisional application No. 61/406,741, filed on Oct. 26, 2010.

(51) Int. Cl.
*C12N 9/24* (2006.01)
*C12N 9/34* (2006.01)
*C12P 7/10* (2006.01)
*C12P 19/02* (2006.01)
*C12P 19/14* (2006.01)

(52) U.S. Cl.
CPC .................. *C12N 9/2428* (2013.01); *C12P 7/10* (2013.01); *C12P 19/02* (2013.01); *C12P 19/14* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| 7,326,548 | B2 | 2/2008 | Udagawa |
| 7,871,800 | B2 | 1/2011 | Landvik |
| 8,148,127 | B2 | 4/2012 | Udagawa |

FOREIGN PATENT DOCUMENTS

| WO | 2006/069289 A2 | 6/2006 |
| WO | 2006/069290 A2 | 6/2006 |
| WO | 2007/134207 A2 | 11/2007 |
| WO | 2007/144424 A2 | 12/2007 |

OTHER PUBLICATIONS

Horst Lyr Archiv Fur Mikrobiologie 35, 258-278 (1960).*
Of Horst Lyr [Archiv Fur Mikrobiologie 35, 258-278 (1960). [English translation].*

* cited by examiner

*Primary Examiner* — Nashaat Nashed
(74) *Attorney, Agent, or Firm* — Michael W. Krenicky

(57) ABSTRACT

The present invention relates to polypeptides having glucoamylase activity and polynucleotides encoding the polypeptides. The invention also relates to nucleic acid constructs, vectors, and host cells comprising the polynucleotides as well as methods of producing and using the polypeptides.

6 Claims, No Drawings

SEQUENCE LISTING

```
<160> NUMBER OF SEQ ID NOS: 22

<210> SEQ ID NO 1
<211> LENGTH: 1722
<212> TYPE: DNA
<213> ORGANISM: Gloeophyllum sepiarium

<400> SEQUENCE: 1
atgtaccgct tccttgtctg tgcgctgggg cttgcggcat cagttctcgc ccagtcggtc      60
gacagctatg ttagcagcga aggtcccata gccaaggcgg gcgtccttgc taacattggg     120
ccgaacggct ccaaggcctc tggcgcatcc gctggtgttg tggtcgcgag ccctagcacg     180
tcggaccccg actattggta cacttggacg cgtgactcgt ccctcgtatt caagtcactt     240
attgaccagt acaccaccgg catcgacagc acgagctctc tgaggactct catcgacgat     300
ttcgtaactg ccgaggctaa tctccagcaa gtctctaacc ctagtggtac cctcaccacc     360
ggtggcttgg gagagcccaa gttcaacgtc gacgaaactg catttactgg tgcatggggt     420
cgaccccaac gcgacggacc tgccctccgc tcgactgcat tgatcacgta cggtaactgg     480
ctgttgtcca acggaaatac gagctatgtt acgagcaatc tgtggccgat catccagaac     540
gaccttggtt atgtcgtgtc atactggaac cagtctacct acgacctctg ggaggaagta     600
gactcgtcat cgttcttcac tactgcagta cagcaccgtg ctctccgtga aggtgcggcc     660
ttcgctaccg ccatcggtca gacttcgcag gtcagcagct atacgactca ggcggacaat     720
cttctgtgct tcttgcagtc ttactggaac ccgagcggtg gttacatcac tgctaacact     780
ggcggcggcc gttccggcaa ggatgccaac acacttctgg catccattca cacgtacgac     840
cccagcgcgg gctgcgacgc tgcgactttc cagccctgct ctgacaaggc actgtcgaac     900
ctgaaggtct acgtcgactc tttccgctcg gtctactcca tcaacagtgg tgtcgcctct     960
aacgctgccg tcgccacggg tcgttatccc gaggatagct accagggtgg aaaccttgg    1020 tacctcacca catttgcggt cgccgagcaa ctctatgatg ctctcaatgt ctgggagtcg    1080
cagggttccc tcgaggtcac ctccacctcc cttgccttct tccagcagtt ctcatccggc    1140
gtcactgctg gcacctactc ttctagctcc agcacataca gcaccctcac gtctgccatc    1200
aagaactttg ccgatggatt tgtcgctatc aatgctaagt acacgccatc caacggtggc    1260
ctggcggaac aatacagcaa gagcgacggt tctcccctta gcgcggtgga cttgacgtgg    1320
agctacgctt cggctttgac ggcgtttgaa gcaaggaaca atactcagtt cgccggctgg    1380
ggcgctgcag gcctgactgt gccttcctct tgctccggca actctggtgg gccgaccgtt    1440
gctgtcacat tcaacgtgaa cgccgagact gtgtggggag agaacatcta tcttactggt    1500
```

```
tccgtcgatg ctctggagaa ctggtcggcc gacaatgccc tcctgctctc atcggctaat    1560
tacccgacct ggagtatcac cgtcaacttg ccggcgagca ctgctattga gtacaagtac    1620
atccgcaaaa ataatggggc cgttacctgg gagtcagacc ccaacaatag catcactact    1680
ccggccagcg gctcgacgac cgagaatgac acttggcgtt ga                      1722
```

<210> SEQ ID NO 2
<211> LENGTH: 573
<212> TYPE: PRT
<213> ORGANISM: Gloeophyllum sepiarium

<400> SEQUENCE: 2

```
Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
        275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335
```

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
    370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
            405                 410                 415

Ser Asn Gly Gly Leu Ala Glu Gln Tyr Ser Lys Ser Asp Gly Ser Pro
        420                 425                 430

Leu Ser Ala Val Asp Leu Thr Trp Ser Tyr Ala Ser Ala Leu Thr Ala
    435                 440                 445

Phe Glu Ala Arg Asn Asn Thr Gln Phe Ala Gly Trp Gly Ala Ala Gly
450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
            485                 490                 495

Tyr Leu Thr Gly Ser Val Asp Ala Leu Glu Asn Trp Ser Ala Asp Asn
        500                 505                 510

Ala Leu Leu Leu Ser Ser Ala Asn Tyr Pro Thr Trp Ser Ile Thr Val
    515                 520                 525

Asn Leu Pro Ala Ser Thr Ala Ile Glu Tyr Lys Tyr Ile Arg Lys Asn
530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
            565                 570

<210> SEQ ID NO 3
<211> LENGTH: 1722
<212> TYPE: DNA
<213> ORGANISM: Gloeophyllum sepiarium

<400> SEQUENCE: 3
atgtaccgct tccttgtctg tgcgctgggg cttgcggcat cagttctcgc ccagtcggtc      60
gacagctatg ttagcagcga aggtcccata gccaaggcgg cgtccttgc taacattggg      120 ccgaacggct ccaaggcctc tggcgcatcc gctggtgttg tggtcgcgag ccctagcacg      180
tcggaccccg actattggta tacttggacg cgtgactcgt ccctcgtttt caagtcactc      240
attgaccagt acaccaccgg catcgacagc acgagctctc tgaggactct catcgacgat      300
ttcgtaactg ccgaggctaa tctccagcaa gtctctaacc ctagtggtac cctcaccacc      360
ggtggcttgg gagagccaaa gttcaacgtc gacgaaactg catttactgg tgcatggggt      420
cgaccccaac gcgacggatc tgccctccgc tcgactgcat tgatcacata cggtaactgg      480
ctgttgtcca acggcaatac gagctatgtt acgagcaaac tgtggccgat catccagaac      540
gatcttggct atgtcgtgtc atactggaac cagtctacct acgatctctg ggaagaagta      600
gactcgtcat cgttcttcac tactgcagtg cagcatcgtg ctctccgcga aggtgcggcg      660
ttcgctacag caatcggtca gacttcgcag gttagcagct ataccacgca ggcggacaat      720
ctcttgtgct tcttgcagtc ttactggaac ccgagcggtg gttacatcac tgctaacact      780

```
ggtggcggcc gttccggcaa ggatgccaac actcttctgg catccattca cacgtacgac      840
cccagcgccg gctgcgacgc tgcgactttc aaccctgct ctgacaaggc actgtcaaac       900
ctgaaagtct atgtcgactc gttccgctcg gtctactcta ttaacagtgg tatcgcctct      960
aacgctgctg tcgccacggg tcggtacccc gaggacagct accagggtgg aaacccttgg     1020
tacctcacca catttgcggt cgccgagcaa ctctatgatg ctctcaatgt ctgggagtcg     1080
cagggttccc tcgaggtcac ttccacctcc cttgccttct tccagcagtt ttcatctggc     1140
gtcactgctg gcacctactc ttctagctcc agcacgtaca gcaccctcac gtctgccatc     1200
aaaagctttg ccgacggatt tgtcactatc aacgctaagt acacgccatc aacggtggc     1260 ctggcggaac aatacagcaa gagcgacggc tctcccctta gcgcggtgga cttgacgtgg     1320
agctacgctt cggctttgac ggcgtttgaa gcaaggaacg atactcagtt cgccggctgg     1380
ggcgctgcag gcctgactgt cccttcctct tgctccggca actcgggtgg gccgaccgtc     1440
gctgttacat tcaacgtgaa cgccgagact gtgtggggag agaacatcta tcttactggt     1500
tcagtcgatg ctctggagaa ctggtcggcc gacaatgccc tcctgctctc atcggctaat     1560
tacccgacct ggagtatcac cgtcaacttg ccggcgagca ctgctattga gtacaagtac     1620
atccgcaaaa ataatggggc cgttacctgg gagtcagacc ccaacaatag tatcactact     1680
ccggccagcg gctcgacgac cgagaatgac acttggcgtt ga                        1722

<210> SEQ ID NO 4
<211> LENGTH: 573
<212> TYPE: PRT
<213> ORGANISM: Gloeophyllym sepiarium

<400> SEQUENCE: 4

Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Ser Ala Leu Arg Ser Thr Ala Leu Ile Thr Tyr Gly Asn Trp
145                 150                 155                 160

Leu Leu Ser Asn Gly Asn Thr Ser Tyr Val Thr Ser Lys Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Ser Phe Phe Thr Thr
        195                 200                 205
```

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Arg Ser Gly Lys Asp Ala Asn Thr Leu
                260                 265                 270

Leu Ala Ser Ile His Thr Tyr Asp Pro Ser Ala Gly Cys Asp Ala Ala
            275                 280                 285

Thr Phe Gln Pro Cys Ser Asp Lys Ala Leu Ser Asn Leu Lys Val Tyr
290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
                340                 345                 350

Asp Ala Leu Asn Val Trp Glu Ser Gln Gly Ser Leu Glu Val Thr Ser
            355                 360                 365

Thr Ser Leu Ala Phe Phe Gln Gln Phe Ser Ser Gly Val Thr Ala Gly
370                 375                 380

Thr Tyr Ser Ser Ser Ser Ser Thr Tyr Ser Thr Leu Thr Ser Ala Ile
385                 390                 395                 400

Lys Ser Phe Ala Asp Gly Phe Val Thr Ile Asn Ala Lys Tyr Thr Pro
                405                 410                 415

Ser Asn Gly Gly Leu Ala Glu Gln Tyr Ser Lys Ser Asp Gly Ser Pro
                420                 425                 430

Leu Ser Ala Val Asp Leu Thr Trp Ser Tyr Ala Ser Ala Leu Thr Ala
            435                 440                 445

Phe Glu Ala Arg Asn Asp Thr Gln Phe Ala Gly Trp Gly Ala Ala Gly
450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
                500                 505                 510

Ala Leu Leu Leu Ser Ser Ala Asn Tyr Pro Thr Trp Ser Ile Thr Val
            515                 520                 525

Asn Leu Pro Ala Ser Thr Ala Ile Glu Tyr Lys Tyr Ile Arg Lys Asn
530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 5
<211> LENGTH: 1722
<212> TYPE: DNA
<213> ORGANISM: Gloeophyllum trabeum

<400> SEQUENCE: 5
atgtaccgct tccttgtctg tgcgctgggg cttgcggcaa cagttctcgc ccagtcggtc    60

```
gacagctatg ttagcagcga aggtcccata gccaaggcgg gcgtccttgc taacattggg      120
ccgaacggct ccaaggcctc tggcgcatcc gctggtgttg tggtcgcgag ccctagcacg      180
tcggaccccg actattggta cacttggacg cgtgactcat ccctcgtttt caagtcactc      240
attgaccagt acaccactgg catcgacagc acgagctctc tgaggactct catcgacgat      300
ttcgtaactg ccgaggctaa tctccagcaa gtctctaacc ctagtggtac cctcaccacc      360
ggtggcttgg gagagcccaa gttcaacgtc gacgaaactg catttactgg tgcatggggt      420
cgaccccaac gcgacggacc tgccctccgc tcgactgcat tgatcacgta cggtaactgg      480
ctgttgtcca acgaaatac gagctatgtt acgagcattc tgtggccgat catccagaac       540
gaccttggtt atgtcgtgtc atattggaac cagtctacct acgacctctg ggaggaagta      600
gactcgtcat cgttcttcac taccgcagta cagcaccgtg ctctccgtga aggtgcggcc      660
ttcgctaccg ccatcggtca gacttcgcag gtcagcagct atacgactca ggcggacaat      720
cttctgtgct tcttgcagtc ttactggaac ccgagcggtg gttacatcac tgctaacact      780
ggcggcggcc gttcgggcaa ggatgccaac acacttctgg catccattca cacgtacgac      840
cccagcgcgg gctgcgacgc tgcgactttc cagccctgct ctgacaaggc actgtcgaac      900
ctgaaggtct acttcgactc tttccgctcg gtctactcca tcaacagtgg tgtcgcctct      960
aacgctgccg tcgccacggg tcgttatccc gaggatagcc accagggtgg aaacccttgg     1020
tacctcacca catttgcggt cgccgagcaa ctctatgatg ctctcaatgt ctgggagtcg     1080
cagggttccc tcgaggtcac ctccacctcc cttgccttct ccagcagtt ctcatccggc      1140 gtcactgctg gcacctactc ttctagctcc agcacataca gcaccctcac gtctgccatc     1200
aagaactttg ccgatggatt tgtcgctatc aatgctaagt acacgccatc caacggtggc     1260
ctggcggaac aatacagcaa gagcgacggt tctcccctta gcgcggtgga cttgacgtgg     1320
agctacgctt cggctttgac ggcgtttgaa gcaaggaaca atactcagtt cgccggctgg     1380
ggcgctgcag gcctgactgt gccttcctct tgctccggca actctggtgg gccgaccgtt     1440
gctgtcacat tcaacgtgaa cgccgagact gtgtggggag agaacatcta tcttactggt     1500
tccgtcgatg ctctggagaa ctggtcggcc gacaatgccc tcctgctctc atcggctaat     1560
tacccgacct ggagtatcac cgtcaacttg ccggcgagca ctgctattga gtacaagtac     1620
atccgcaaaa ataatgggc cgttacctgg gagtcagacc ccaacaatag catcactact      1680
ccggccagcg gctcgacgac cgagaatgac acttggcgtt aa                         1722

<210> SEQ ID NO 6
<211> LENGTH: 573
<212> TYPE: PRT
<213> ORGANISM: Gloeophyllum trabeum

<400> SEQUENCE: 6

Met Tyr Arg Phe Leu Val Cys Ala Leu Gly Leu Ala Ala Thr Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80
```

```
Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Ile Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Ser Phe Phe Thr Thr
            195                 200                 205

Ala Val Gln His Arg Ala Leu Arg Glu Gly Ala Ala Phe Ala Thr Ala
            210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
                275                 280                 285

Thr Phe Gln Pro Cys Ser Asp Lys Ala Leu Ser Asn Leu Lys Val Tyr
            290                 295                 300

Phe Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
            355                 360                 365

Thr Ser Leu Ala Phe Phe Gln Gln Phe Ser Ser Gly Val Thr Ala Gly
            370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
            435                 440                 445

Phe Glu Ala Arg Asn Asn Thr Gln Phe Ala Gly Trp Gly Ala Ala Gly
450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495
```

```
Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
            515                 520                 525

Asn Leu Pro Ala Ser Thr Ala Ile Glu Tyr Lys Tyr Ile Arg Lys Asn
            530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
            565                 570

<210> SEQ ID NO 7
<211> LENGTH: 1722
<212> TYPE: DNA
<213> ORGANISM: Gloeophyllum sepiarium

<400> SEQUENCE: 7
```

| | | | | | |
|---|---|---|---|---|---|
| atgtaccgct | tccttgtctg | tgcgctcggg | cttgcggcgt | cagttctcgc | ccagtcggtc | 60 |
| gacagctatg | ttagcagcga | aggtcccata | gccaaggcgg | gcgtccttgc | taacattgga | 120 |
| ccgaacgggct | ccaaggcctc | tggcgcatcc | gctggtgttg | tggtcgcgag | ccctagcacg | 180 |
| tcggaccccg | actattggta | cacttggacg | cgtgactcat | ccctcgtttt | caagtcactc | 240 |
| attgaccagt | acaccactgg | catcgacagc | acgagctctc | tgaggactct | catcgacgat | 300 |
| tcgtaactg | ccgaggctaa | tctccagcaa | gtctctaacc | ctagtggtac | cctcaccacc | 360 |
| ggtggcttgg | gagagcccaa | gttcaacgtc | gacgaaactg | catttactgg | tgcatggggt | 420 |
| cgaccccaac | gcgacggacc | tgccctccgc | tcgactgcat | tgatcacgta | cggtaactgg | 480 |
| ctgttgtcca | acggaaatac | gagctatgtt | acgagcaatc | tgtggccgat | catccagaac | 540 |
| gaccttggtt | atgtcgtgtc | atactggaac | cagtctacct | acgacctctg | ggaggaagta | 600 |
| gactcgtcat | cgttcttcac | tactgcagtg | cagcatcgtg | ctctccgcga | aggtgcggcg | 660 |
| ttcgccaccg | cgatcggtca | gacttcgcag | gttagcagct | ataccacgca | ggcggacaat | 720 |
| ctcctgtgct | ttttgcagtc | ttactggaac | ccgagcggtg | gttacatcac | tgctaacact | 780 |
| ggtggcggcc | gttccggcaa | ggatgccaac | actcttctgg | catccattca | cacgtacgac | 840 |
| cccagcgccg | gctgcgatgc | tgccactttc | caaccctgct | ctgacaaggc | actgtccaac | 900 |
| ctgaaagtct | acgtcgactc | gttccgctcg | gtctactcta | ttaacagtgg | tatcgcctct | 960 |
| aacgccgctg | tcgccacggg | tcggtacccc | gaggacagct | accagggtgg | aaacccttgg | 1020 |
| tatctcacca | catttgcggt | cgccgagcaa | ctctatgatg | ctctcaatgt | ctgggagttg | 1080 |
| cagggttccc | tcgaggtcac | ctccacctcc | cttgccttct | ccagcagttt | ctcgtccggc | 1140 |
| gtcactgctg | gcacctactc | ttctagctcc | agcacataca | gcaccctcac | gtctgccatc | 1200 |
| aagagctttg | ccgatggatt | tgtcgctatc | aatgctaagt | acacgccatc | caacggtggc | 1260 |
| ctggcggaac | aatatagcaa | gagcgacggc | tctccccta | gcgcggtgga | cttgacgtgg | 1320 |
| agctacgctt | cggctttgac | ggcgtttgaa | gcaaggaacg | cactcagtt | cgccggctgg | 1380 |
| ggcgctgcaa | gcctgactgt | gccttcctct | tgctccggca | actctggtgg | gccgaccgtc | 1440 |
| gctgtcacat | tcaacgtgaa | cgccgagact | gtgtggggag | agaacatcta | tcttactggt | 1500 |
| tccgtcgatg | ctctggagaa | ctggtcggcc | gacaatgccc | tcctgctctc | atcggctaac | 1560 |
| tacccgacct | ggagtatcac | cgtcaacttg | ccggcgagca | ctgccattga | gtacaagtac | 1620 |
| atccgcaaaa | ataatggggc | agttacctgg | gagtcagacc | ccaacaatag | catcactact | 1680 | ccggccagcg gctcgacgac cgagaatgac acttggcgtt aa         1722

<210> SEQ ID NO 8
<211> LENGTH: 573
<212> TYPE: PRT
<213> ORGANISM: Gloeophyllum sepiarium

<400> SEQUENCE: 8

Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
        275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Leu Gln Gly Ser Leu Glu Val Thr Ser
        355                 360                 365

```
Thr Ser Leu Ala Phe Phe Gln Gln Phe Ser Ser Gly Val Thr Ala Gly
        370                 375                 380

Thr Tyr Ser Ser Ser Ser Thr Tyr Ser Thr Leu Thr Ser Ala Ile
385                 390                 395                 400

Lys Ser Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asp Thr Gln Phe Ala Gly Trp Gly Ala Ala Ser
450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570
```

<210> SEQ ID NO 9
<211> LENGTH: 1722
<212> TYPE: DNA
<213> ORGANISM: Gloeophyllum sepiarium

<400> SEQUENCE: 9

```
atgtaccgct tccttgtctg tgcgctcggg cttgctgcaa cagttctcgc ccagtcggtc      60
gacagctatg ttagcagcga agggcccgta gccaaggcgg gcgtccttgc taacattgga     120
ccgaacggct ccaaggcctc tggcgcgtcc gccggtgttg tggtagcgag cccgagcacg     180
tccgaccccg actattggta cacttggacg cgtgactcgt ccctcgtttt caagtcactc     240
attgaccagt acaccaccgg catcgacagc acgagctctc tgaggactct catcgacgat     300
ttcgtaactg ccgaggctaa tctccagcaa gtctctaacc ctagtggtac cctcactacc     360
ggtggcttgg gagagccaaa gttcaacgtc gacgaaactg catttactgg tgcatggggt     420
cgaccccaac gcgacggacc tgccctccgt tcgactgcat tgatcacata cggtaattgg     480
ctgttgtcca acggaaatac gagctatgtt acgagcaatc tgtggccgat catccagaac     540
gaccttggtt atgtcgtgtc atactggaac cagtctacct acgacctctg gaggaagta      600
gactcgtcat cgttcttcac tactgcagta cagcaccgtg ctctccgtga aggtgcggcg     660
ttcgctaccg ccatcggtca gacttcgcag gtcagcagct atacgactca ggcggacaat     720
cttctgtgct tcttgcagtc atactggaac ccgagcggtg ttatatcac tgctaacact      780
ggtggcggcc gttccggcaa ggatgccaac actcttctgg catccattca cacatacgat     840
cccagcgccg gctgcgacgc tgccactttc cagccctgct ctgacaaggc gctgtcgaat     900
ctgaaggtct acgtcgactc cttccgctca atctactcca tcaacagtgg tatcgcctct     960
```

```
aacgccgccg tcgccacggg tcgttacccc gaggacagct accagggtgg aaacccttgg   1020
tacctcacca catttgcggt cgccgagcaa ctctatgatg ctctcaatgt ctgggagtcg   1080
cagggttccc tcgaggtcac ctccacctcc cttgccttct tccagcagtt ctcatccggc   1140
gtcactgctg caacctactc ttctagctcc agcacataca gcaccctcac gtctgccatc   1200
aagagctttg ccgatggatt tgtcgctatc aatgctaagt acacgccatc caacggtggc   1260
ctggcggaac aatatagcaa gagcgacggc tctcccctta gcgcggtgga cttgacgtgg   1320
agctacgctt cggctttgac ggcgtttgaa gcaaggaacg acactcagtt cgccggctgg   1380
ggcgctgcag gcctgactgt gccttcctct tgctccggca actctggtgg ccgaccgtc    1440 gcggtcacat tcaacgtgaa cgccgagact gtgtggggag agaacatcta tcttactggt   1500
tccgtcgatg ctctggagaa ctggtcggcc gacaatgccc tcctgctctc atcggctaac   1560
tacccgacct ggagtatcac cgtcaacttg ccggcgagca ctgccattga gtacaagtac   1620
atccgcaaaa ataatggggc cgtcacctgg gagtcagacc ccaacaatag catcactact   1680
ccggccagcg gctcgacgac cgagaatgac acttggcgtt aa                      1722
```

<210> SEQ ID NO 10
<211> LENGTH: 573
<212> TYPE: PRT
<213> ORGANISM: Gloeophyllum sepiarium

<400> SEQUENCE: 10

```
Met Tyr Arg Phe Leu Val Cys Ala Leu Gly Leu Ala Ala Thr Val Leu
1               5                   10                  15

Ala Gln Ser Val Asp Ser Tyr Val Ser Glu Gly Pro Val Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Ser Tyr Trp Asn Gln Ser
            180                 185                 190

Thr Tyr Asp Leu Trp Glu Glu Val Asp Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240
```

```
Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
        275                 280                 285

Thr Phe Gln Pro Cys Ser Asp Lys Ala Leu Ser Asn Leu Lys Val Tyr
    290                 295                 300

Val Asp Ser Phe Arg Ser Ile Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
    370                 375                 380

Thr Tyr Ser Ser Ser Ser Ser Thr Tyr Ser Thr Leu Thr Ser Ala Ile
385                 390                 395                 400

Lys Ser Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asp Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 11
<211> LENGTH: 1722
<212> TYPE: DNA
<213> ORGANISM: Gloeophyllum sp

<400> SEQUENCE: 11
atgtaccgct tccttgtctg tgccctcggg cttgctgcaa cagttctcgc ccagtcggtc      60
gacagctatg ttagcagcga agggcccgta gccaaggcgg gcgtcctttgc taacattgga    120 ccgaacggct ccaaggcctc tggcgcgtcc gccggtgttg tggtagcgag cccgagcacg    180
tcggaccccg actattggta cacttggacg cgtgactcgt ccctcgtttt caagtcactc    240
```

```
attgaccagt acaccaccgg catcgacagc acgagctctc tgaggactct catcgacgat    300
ttcgtaactg ccgaggctaa tctccagcaa gtctctaacc ctagtggtac cctcactacc    360
ggtggcttgg gagagccaaa gttcaacgtc gacgaaactg catttactgg tgcatggggt    420
cgacccaac  gcgacggacc tgccctccgt tcgactgcat tgatcacata cggtaactgg    480
ctgttgtcca acggaaatac gagctatgtt acgagcaatc tgtggccgat catccagaac    540
gaccttggtt atgtcgtgtc atactggaac cagtctacct acgacctctg ggaggaagta    600
gactcgtcat cgttcttcac tactgcagta cagcaccgtg ctctccgtga aggtgcggcg    660
ttcgctaccg ccatcggtca gacttcgcag gtcagcagct atacgactca gcggacaat    720
cttctgtgct tcttgcagtc atactggaac ccgagcggtg gttatatcac tgctaacact    780
ggtggcggcc gttccggcaa ggatgccaac actcttctgg catccattca cacatacgat    840
cccagcgccg gctgcgacgc tgccactttc agccctgct  ctgacaaggc gctgtcgaat    900
ctgaaggtct acgtcgactc cttccgctcg atctactcca tcaacagtgg tatcgcctct    960
aacgccgccg tcgccacggg tcgttacccc gaggacagct accagggtgg aaacccttgg   1020
tacctcacca catttgcggt cgccgagcaa ctctatgatg ctctcaatgt ctgggagtcg   1080
cagggttccc tcgaggtcac ctccacctcc cttgccttct ccagcagtt  ctcatccggc   1140
gtcactgctg gcacctactc ttctagctcc agcacataca gcaccctcac gtctgccatc   1200
aagagctttg ccgatggatt tgtcgctatc aatgctaagt acacgccatc caacggtggc   1260
ctggcggaac aatatagcaa gagcgacggc tctcccctta gcgcggtgga cttgacgtgg   1320
agctacgctt cggctttgac ggcgtttgaa gcaaggaacg acactcagtt cgccggctgg   1380
ggcgctgcag gcctgactgt gccttcctct tgctccggca actctggtgg gccgaccgtc   1440
gctgtcacat tcaacgtgaa cgccgagact gtgtggggag agaacatcta tcttactggt   1500
tccgtcgatg ctctggagaa ctggtcggcc gacaatgccc tcctgctctc atcggttaac   1560
tacccgacct ggagtatcac cgtcaacttg ccggcgagca ctgccattga gtacaagtac   1620
atccgcaaaa ataatggggc cgtcacctgg gagtcagatc ccaacaatag catcactact   1680
ccggccagcg gctcgacgac cgagaatgac acttggcgtt aa                      1722
```

<210> SEQ ID NO 12
<211> LENGTH: 573
<212> TYPE: PRT
<213> ORGANISM: Gloeophyllum sp

<400> SEQUENCE: 12

```
Met Tyr Arg Phe Leu Val Cys Ala Leu Gly Leu Ala Ala Thr Val Leu
1               5                   10                  15

Ala Gln Ser Val Asp Ser Tyr Val Ser Ser Glu Gly Pro Val Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110
```

```
Asn Pro Ser Gly Thr Leu Thr Thr Gly Gly Leu Gly Glu Pro Lys Phe
            115                 120                 125

Asn Val Asp Glu Thr Ala Phe Thr Gly Ala Trp Gly Arg Pro Gln Arg
        130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Ser Tyr Trp Asn Gln Ser
                180                 185                 190

Thr Tyr Asp Leu Trp Glu Glu Val Asp Ser Ser Ser Phe Phe Thr Thr
        195                 200                 205

Ala Val Gln His Arg Ala Leu Arg Glu Gly Ala Ala Phe Ala Thr Ala
        210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
                260                 265                 270

Leu Ala Ser Ile His Thr Tyr Asp Pro Ser Ala Gly Cys Asp Ala Ala
                275                 280                 285

Thr Phe Gln Pro Cys Ser Asp Lys Ala Leu Ser Asn Leu Lys Val Tyr
                290                 295                 300

Val Asp Ser Phe Arg Ser Ile Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
                340                 345                 350

Asp Ala Leu Asn Val Trp Glu Ser Gln Gly Ser Leu Glu Val Thr Ser
                355                 360                 365

Thr Ser Leu Ala Phe Phe Gln Gln Phe Ser Ser Gly Val Thr Ala Gly
        370                 375                 380

Thr Tyr Ser Ser Ser Ser Ser Thr Tyr Ser Thr Leu Thr Ser Ala Ile
385                 390                 395                 400

Lys Ser Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
                420                 425                 430

Leu Ser Ala Val Asp Leu Thr Trp Ser Tyr Ala Ser Ala Leu Thr Ala
                435                 440                 445

Phe Glu Ala Arg Asn Asp Thr Gln Phe Ala Gly Trp Gly Ala Ala Gly
        450                 455                 460

Leu Thr Val Pro Ser Ser Cys Ser Gly Asn Ser Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
                500                 505                 510

Ala Leu Leu Leu Ser Ser Val Asn Tyr Pro Thr Trp Ser Ile Thr Val
                515                 520                 525

Asn Leu Pro Ala Ser Thr Ala Ile Glu Tyr Lys Tyr Ile Arg Lys Asn
```

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 13
<211> LENGTH: 1722
<212> TYPE: DNA
<213> ORGANISM: Gloeophyllum trabeum

<400> SEQUENCE: 13

| | | | | | |
|---|---|---|---|---|---|
| atgtaccgct | tccttgtctg | tgcgctgggg | cttgcggcgt | cagttctcgc | ccagtcggtc | 60 |
| gacagctatg | ttagcagcga | aggtcccata | gccaaggcgg | gcgtccttgc | taacattgga | 120 |
| ccgaacggct | ccaaggcctc | tggcgcatcc | gctggcgttg | tggtcgcaag | cccaagcacg | 180 |
| tcggaccccg | actattggta | cacttggacg | cgtgactcgt | ccctcgtttt | caagtcactc | 240 |
| attgaccagt | acaccaccgg | catcgacggc | acgagctctc | tgaggactct | catcgacgat | 300 |
| ttcgtaactg | ccgaggctaa | tcttcagcaa | gtctctaacc | ctagtggtac | cctcaccacc | 360 |
| ggtggcttgg | gagagccaaa | gttcaacgtc | gacgaaactg | catttactgg | tgcatggggt | 420 |
| cgaccccaac | gtgacggacc | tgccctccgc | tcgactgcgc | tgatcacata | cggtaactgg | 480 |
| ctgttgtcca | acgggaatac | gagctatgtt | acgagcaatc | tgtggccgat | catccagaac | 540 |
| gaccttggtt | atgtcgtgtc | atactggaac | cagtccacgt | acgatctctg | gaggaagta | 600 |
| gactcgtcgt | cattcttcac | tactgcagtg | cagcaccgtg | ctctccgtga | aggagcggcg | 660 |
| ttcgctaccg | ctatcggtca | gacttcgcag | gttagcagct | atacgactca | ggcggacaat | 720 |
| cttctgtgct | tcttgcagtc | ttactggaac | ccgagtggtg | gttacatcac | tgctaacact | 780 |
| ggcggcggcc | gttccggcaa | ggatgccaac | actcttctgg | catccattca | tacgtacgac | 840 |
| cccagcgccg | gctgcgacgc | tgcgactttc | agccctgct | ctgacaaggc | attgtcgaac | 900 |
| ctgaaagtct | acgttgactc | tttccgctcg | gtctattcca | tcaacagtgg | tatcgcctct | 960 |
| aacgccgccg | tcgccacggg | tcgttacccc | gaggacagct | accagggtgg | aaatccttgg | 1020 |
| tacctcacca | catttgcggt | cgccgagcaa | ctctatgatg | ctctcaatgt | ctgggagtcg | 1080 |
| cagggctccc | tcgaggtcac | ctccacctcc | cttgccttct | tccagcagtt | ctcatccggt | 1140 |
| gtcactgctg | gcacctactc | ttctagctcc | agcacgtaca | gcaccctcac | gtctgctatc | 1200 |
| aagagctttg | ccgatggatt | tgtcgctgtc | aacgctaagt | acacgccatc | caacggtggc | 1260 |
| ctggcggaac | aatacagcaa | gagcgacggt | tctcccctta | gcgcggtgga | cttgacgtgg | 1320 |
| agctacgctt | cggctttgac | ggcgtttgaa | gcaaggaaca | cactcagtt | cgccggctgg | 1380 |
| ggcgctgcag | gcctgactgt | gccttcctct | tgctccggca | actctggtgg | gccgaccgtc | 1440 |
| gctgttacat | tcaacgtgaa | cgccgagact | gtgtggggag | agaacatcta | tcttactggt | 1500 |
| tcagtcgatg | ctctggagaa | ctggtcggcc | gacaatgccc | tcctgctctc | atcggctaat | 1560 |
| tacccgacct | ggagtatcac | cgtcaacttg | ccggcgagca | ctgctattga | gtacaagtac | 1620 |
| atccgcaaaa | ataatggggc | cgttacctgg | gagtcagacc | ccaacaatag | catcactact | 1680 |
| ccggctagcg | gctcgacgac | cgagaatgac | acttggcgtt | aa | | 1722 |

<210> SEQ ID NO 14
<211> LENGTH: 573
<212> TYPE: PRT
<213> ORGANISM: Gloeophyllum trabeum

<400> SEQUENCE: 14

```
Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Gly Thr Ser Ser Leu Arg Thr
                85                  90                  95

Leu Ile Asp Asp Phe Val Thr Ala Glu Ala Asn Leu Gln Gln Val Ser
                100                 105                 110

Asn Pro Ser Gly Thr Leu Thr Gly Gly Leu Gly Glu Pro Lys Phe
            115                 120                 125

Asn Val Asp Glu Thr Ala Phe Thr Gly Ala Trp Gly Arg Pro Gln Arg
130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Asn Trp Gln Ser
                180                 185                 190

Thr Tyr Asp Leu Trp Glu Glu Val Asp Ser Ser Phe Phe Thr Thr
            195                 200                 205

Ala Val Gln His Arg Ala Leu Arg Glu Gly Ala Ala Phe Ala Thr Ala
            210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
        275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
    370                 375                 380

Thr Tyr Ser Ser Ser Ser Thr Tyr Ser Thr Leu Thr Ser Ala Ile
385                 390                 395                 400

Lys Ser Phe Ala Asp Gly Phe Val Ala Val Asn Ala Lys Tyr Thr Pro
```

```
                    405                 410                 415
Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
            435                 440                 445

Phe Glu Ala Arg Asn Asn Thr Gln Phe Ala Gly Trp Gly Ala Ala Gly
            450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
            515                 520                 525

Asn Leu Pro Ala Ser Thr Ala Ile Glu Tyr Lys Tyr Ile Arg Lys Asn
            530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
            565                 570
```

<210> SEQ ID NO 15
<211> LENGTH: 1731
<212> TYPE: DNA
<213> ORGANISM: Gloeophyllum trabeum

<400> SEQUENCE: 15

```
atgtaccgct tccttgtctg tgctctcggg cttctggga cagtcctcgc tcagtcagtc      60
gacagttatg tcggcagcga aggccccata gcaaaggccg gcgtccttgc aacattggg     120
ccgaatggcc caaggcctc tggtgcagcc gccggcgtgg tggtggctag ccccagcaag     180
tcggatcccg actattggta cacttggacg cgtgactcgt cactcgtttt caagtctctc     240
attgatcagt acaccactgg tatcgacagc acgagttcgc tgaggtctct gatagacagt     300
ttcgttattg ccgaggccaa cattcagcag gtctctaatc ccagcggcac tcttactacc     360
ggcggcttgg gagagccaaa attcaatgtc gatgaaactg cattcaccgg tgcatggggt     420
cgacccccagc gcgacggacc tgcgctccgt gcgactgctt tgatcaccta cggtaactgg     480
ctcttgtcaa cgggaacac gacctgggtt accagtacgc tgtggccgat catccagaac     540
gatctcaact acgtcgttca gtactggaac cagaccacct tcgacctctg ggaagaagtg     600
aactcttcct cgttcttcac cactgcagtg cagcaccgtg ccttgcgcga aggcgcagca     660
ttcgctacca agatcggtca gacctcctcg gtcagcagct acacaaccca agcggcgaat     720
ctactttgct ttttgcagtc ttactggaac cccacttccg gatatatcac cgctaacact     780
ggcggtggtc ggtccggcaa ggacgccaac accctcttgg catccatcca cacttacgac     840
cccagcgcgg gctgcgatgc cacgaccttc cagccctgct ccgacaaagc cctctcgaat     900
ctgaaggttt acgtcgactc cttccgttct gtcactccca tcaacagcgg tattgcctct     960
aacgccgctg tagccactgg tcgctacccg gaagacagct accagggcgg gaacccatgg    1020
tacctcacta cgttccgcgt cgccgagcag ctctatgacg ccctcaatgt ctgggctgct    1080
cagggctccc tcaatgtcac ctccatctcc ctccccttct tccagcagtt ctcctctagt    1140
gtcactgccg gcacttatgc ttcgagctcc accacttaca cgactctgac ctccgccatt    1200
```

-continued

```
aagagcttcg cggatggatt cgtcgctatc aacgcccagt acacgccgtc caacggtggc      1260
ctcgctgagc agttcagcag gagcaacggc tctcccgtca gcgctgttga cttgacatgg      1320
agctatgcat ccgcattgac cgcgtttgaa gcgaggaata atactcagtt cgccggctgg      1380
ggcgcggtag gtttgactgt gccgacctcg tgctccagca acgtggtgg aggcggagga       1440 tcaactgtcg ccgtgacgtt caacgtgaac gcccaaacgg tttggggcga aaacatctac      1500
atcactggct cggttgacgc tctgagtaac tggtctcctg caacgccct cttgctctcg       1560 tctgccaact acccgacctg gagcattacc gtgaatttac ccgcgagcac tgccattcag      1620
tataagtata tccgcaagaa caacggagct gtcacctggg aatccgatcc caacaacagc      1680
ataactactc cagccagcgg ctccgtgacc gagaatgaca cttggcgtta a               1731
```

<210> SEQ ID NO 16
<211> LENGTH: 576
<212> TYPE: PRT
<213> ORGANISM: Gloeophyllum trabeum

<400> SEQUENCE: 16

```
Met Tyr Arg Phe Leu Val Cys Ala Leu Gly Leu Leu Gly Thr Val Leu
1               5                   10                  15

Ala Gln Ser Val Asp Ser Tyr Val Gly Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ala Ala Gly Val Val Val Ala Ser Pro Ser Lys Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Ser
                85                  90                  95

Leu Ile Asp Ser Phe Val Ile Ala Glu Ala Asn Ile Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ala Thr Ala Leu Ile Thr Tyr Gly Asn Trp
145                 150                 155                 160

Leu Leu Ser Asn Gly Asn Thr Thr Trp Val Thr Ser Thr Leu Trp Pro
                165                 170                 175

Ile Ile Gln Asn Asp Leu Asn Tyr Val Val Gln Tyr Trp Asn Gln Thr
            180                 185                 190

Thr Phe Asp Leu Trp Glu Glu Val Asn Ser Ser Phe Phe Thr Thr
        195                 200                 205

Ala Val Gln His Arg Ala Leu Arg Glu Gly Ala Ala Phe Ala Thr Lys
    210                 215                 220

Ile Gly Gln Thr Ser Ser Val Ser Ser Tyr Thr Thr Gln Ala Ala Asn
225                 230                 235                 240

Leu Leu Cys Phe Leu Gln Ser Tyr Trp Asn Pro Thr Ser Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Thr
```

|     |     |     |     |     | 275 |     |     |     | 280 |     |     |     |     | 285 |
| --- | --- | --- | --- | --- | --- | --- | --- | --- | --- | --- | --- | --- | --- | --- |

Thr Phe Gln Pro Cys Ser Asp Lys Ala Leu Ser Asn Leu Lys Val Tyr
290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Ala Ala Gln Gly Ser Leu Asn Val Thr Ser
                355                 360                 365

Ile Ser Leu Pro Phe Phe Gln Gln Phe Ser Ser Val Thr Ala Gly
370                 375                 380

Thr Tyr Ala Ser Ser Thr Thr Tyr Thr Thr Leu Thr Ser Ala Ile
385                 390                 395                 400

Lys Ser Phe Ala Asp Gly Phe Val Ala Ile Asn Ala Gln Tyr Thr Pro
                405                 410                 415

Ser Asn Gly Gly Leu Ala Glu Gln Phe Ser Arg Ser Asn Gly Ser Pro
            420                 425                 430

Val Ser Ala Val Asp Leu Thr Trp Ser Tyr Ala Ser Ala Leu Thr Ala
                435                 440                 445

Phe Glu Ala Arg Asn Asn Thr Gln Phe Ala Gly Trp Gly Ala Val Gly
450                 455                 460

Leu Thr Val Pro Thr Ser Cys Ser Ser Asn Ser Gly Gly Gly Gly
465                 470                 475                 480

Ser Thr Val Ala Val Thr Phe Asn Val Asn Ala Gln Thr Val Trp Gly
                485                 490                 495

Glu Asn Ile Tyr Ile Thr Gly Ser Val Asp Ala Leu Ser Asn Trp Ser
            500                 505                 510

Pro Asp Asn Ala Leu Leu Leu Ser Ser Ala Asn Tyr Pro Thr Trp Ser
                515                 520                 525

Ile Thr Val Asn Leu Pro Ala Ser Thr Ala Ile Gln Tyr Lys Tyr Ile
530                 535                 540

Arg Lys Asn Asn Gly Ala Val Thr Trp Glu Ser Asp Pro Asn Asn Ser
545                 550                 555                 560

Ile Thr Thr Pro Ala Ser Gly Ser Val Thr Glu Asn Asp Thr Trp Arg
                565                 570                 575

<210> SEQ ID NO 17
<211> LENGTH: 1731
<212> TYPE: DNA
<213> ORGANISM: Gloeophyllum trabeum

<400> SEQUENCE: 17

| | | |
|---|---|---|
| atgtaccgct tccttgtctg tgctctcggg cttctgggga cagtcctcgc tcagtcagtc | 60 |
| gacagttatg tcggcagcga aggccccata gcaaaggccg cgtccttgc caacattggg | 120 |
| ccgaacggct caaaggcctc tggtgcagcc gccggcgtgg tggtggctag ccccagcaag | 180 |
| tcggatcccg actattggta cacttggacg cgtgactcgt cactcgtttt caagtctctc | 240 |
| attgatcagt acaccactgg tatcgacagc acgagttcgt tgaggtctct gatagacagt | 300 |
| ttcgttattg ccgaggccaa cattcagcag gtctctaatc ccagcggcac tcttactacc | 360 |
| ggcggcttgg gagagccaaa attcaatgtc gatgaaactg cattcaccgg tgcatggggt | 420 |
| cgaccccagc gcgacggacc tgcgctccgt gcgactgctt tgatcaccta cggtaactgg | 480 |

```
ctcttgtcaa acgggaacac gacctgggtt accagtacgc tgtggccgat catccagaac    540
gatctcaact acgtcgttca gtactggaac cagaccacct tcgacctctg gaagaagtg    600
aactcttcct cgttcttcac cactgcagtg cagcaccgtg ccttgcgcga aggcgcagca    660
ttcgctacca agatcggtca gacctcctcg gtcagcagct acacaaccca agcggcgaat    720
ctactttgct ttttgcagtc ttactggaac cccacttccg gatatatcac cgctaacact    780
ggcggtggtc ggtccggcaa ggacgccaac accctcttgg catccatcca cacttacgac    840
cccagcgcgg gctgcgatgc cacgaccttc agccctgct ccgacaaagc cctctcgaat    900
ctgaaggttt acgtcgactc cttccgttct gtctactcca tcaacagcgg tattgcctct    960
aacgccgctg tcgccactgg tcgctacccg aagacagct accagggcgg gaacccatgg   1020
tacctcacta cgttcgccgt cgccgagcag ctctatgacg ccctcaatgt ctgggctgct   1080
cagggctccc tcaatgtcac ctccatctcc ctcccttct tccagcagtt ctcctctagt   1140
gtcactgccg gcacttacgc ttcgagctcc accacttaca cgactctgac ctccgccatt   1200
aagagcttcg cggatggatt cgtcgctatc aacgcccagt acacgccgtc caacggtggc   1260
ctcgctgagc agttcagcag gagcaacggc gctcccgtca cgctgttga tttgacatgg   1320
agctatgcat ctgcattgac cgcgtttgaa gcgaggaata atactcagtt cgccggctgg   1380
ggcgcggtag gtttgactgt gccgacctcg tgctccagca acagtggtgg aggcggagga   1440
tcgactgtcg ccgtgacgtt caacgtgaac gcccaaacgg tttggggcga aacatctac   1500
atcactggct cggttgacgc tctgagtaac tggtctcccg acaacgccct cttgctctcg   1560
tctgccaact acccgacctg gagcattacc gtgaatttac ccgcgagcac tgccattcag   1620
tataagtata tccgcaagaa caacggagct gtcacctggg aatccgatcc caacaacagc   1680
ataactactc cagccagcgg ctccgtgacc gagaatgaca cttggcgtta a             1731
```

<210> SEQ ID NO 18
<211> LENGTH: 576
<212> TYPE: PRT
<213> ORGANISM: Gloeophyllum trabeum

<400> SEQUENCE: 18

```
Met Tyr Arg Phe Leu Val Cys Ala Leu Gly Leu Gly Thr Val Leu
1               5                   10                  15

Ala Gln Ser Val Asp Ser Tyr Val Gly Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ala Ala Gly Val Val Val Ala Ser Pro Ser Lys Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Ser Ser Leu Arg Ser
                85                  90                  95

Leu Ile Asp Ser Phe Val Ile Ala Glu Ala Asn Ile Gln Gln Val Ser
            100                 105                 110

Asn Pro Ser Gly Thr Leu Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ala Thr Ala Leu Ile Thr Tyr Gly Asn Trp
```

```
            145                 150                 155                 160
Leu Leu Ser Asn Gly Asn Thr Thr Trp Val Thr Ser Thr Leu Trp Pro
                165                 170                 175

Ile Ile Gln Asn Asp Leu Asn Tyr Val Val Gln Tyr Trp Asn Gln Thr
                180                 185                 190

Thr Phe Asp Leu Trp Glu Glu Val Asn Ser Ser Phe Thr Thr
                195                 200             205

Ala Val Gln His Arg Ala Leu Arg Glu Gly Ala Ala Phe Ala Thr Lys
            210                 215                 220

Ile Gly Gln Thr Ser Ser Val Ser Ser Tyr Thr Thr Gln Ala Ala Asn
225                 230                 235                 240

Leu Leu Cys Phe Leu Gln Ser Tyr Trp Asn Pro Thr Ser Gly Tyr Ile
                245                 250                 255

Thr Ala Asn Thr Gly Gly Gly Arg Ser Gly Lys Asp Ala Asn Thr Leu
                260                 265                 270

Leu Ala Ser Ile His Thr Tyr Asp Pro Ser Ala Gly Cys Asp Ala Thr
            275                 280                 285

Thr Phe Gln Pro Cys Ser Asp Lys Ala Leu Ser Asn Leu Lys Val Tyr
            290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
                340                 345                 350

Asp Ala Leu Asn Val Trp Ala Ala Gln Gly Ser Leu Asn Val Thr Ser
            355                 360                 365

Ile Ser Leu Pro Phe Phe Gln Gln Phe Ser Ser Val Thr Ala Gly
            370                 375                 380

Thr Tyr Ala Ser Ser Ser Thr Thr Tyr Thr Thr Leu Thr Ser Ala Ile
385                 390                 395                 400

Lys Ser Phe Ala Asp Gly Phe Val Ala Ile Asn Ala Gln Tyr Thr Pro
                405                 410                 415

Ser Asn Gly Gly Leu Ala Glu Gln Phe Ser Arg Ser Asn Gly Ala Pro
            420                 425                 430

Val Ser Ala Val Asp Leu Thr Trp Ser Tyr Ala Ser Ala Leu Thr Ala
            435                 440                 445

Phe Glu Ala Arg Asn Asn Thr Gln Phe Ala Gly Trp Gly Ala Val Gly
            450                 455                 460

Leu Thr Val Pro Thr Ser Cys Ser Ser Asn Ser Gly Gly Gly Gly
465                 470                 475                 480

Ser Thr Val Ala Val Thr Phe Asn Val Asn Ala Gln Thr Val Trp Gly
                485                 490                 495

Glu Asn Ile Tyr Ile Thr Gly Ser Val Asp Ala Leu Ser Asn Trp Ser
                500                 505                 510

Pro Asp Asn Ala Leu Leu Leu Ser Ser Ala Asn Tyr Pro Thr Trp Ser
            515                 520                 525

Ile Thr Val Asn Leu Pro Ala Ser Thr Ala Ile Gln Tyr Lys Tyr Ile
            530                 535                 540

Arg Lys Asn Asn Gly Ala Val Thr Trp Glu Ser Asp Pro Asn Asn Ser
545                 550                 555                 560

Ile Thr Thr Pro Ala Ser Gly Ser Val Thr Glu Asn Asp Thr Trp Arg
                565                 570                 575
```

<210> SEQ ID NO 19
<211> LENGTH: 1857
<212> TYPE: DNA
<213> ORGANISM: Talaromyces emersonii

<400> SEQUENCE: 19

| | | | | | |
|---|---|---|---|---|---|
| atggcgtccc | tcgttgctgg | cgctctctgc | atcctgggcc | tgacgcctgc | tgcatttgca | 60 |
| cgagcgcccg | ttgcagcgcg | agccaccggt | tccctggact | cctttctcgc | aaccgaaact | 120 |
| ccaattgccc | tccaaggcgt | gctgaacaac | atcgggccca | atggtgctga | tgtggcagga | 180 |
| gcaagcgccg | gcattgtggt | tgccagtccg | agcaggagcg | acccaaatta | tttctactcc | 240 |
| tggacacgtg | acgcagcgct | cacggccaaa | tacctcgtcg | acgccttcat | cgcgggcaac | 300 |
| aaggacctag | agcagaccat | ccagcagtac | atcagcgcgc | aggcgaaggt | gcaaactatc | 360 |
| tccaatccgt | ccggagattt | atccaccggt | ggcttaggtg | agcccaagtt | caatgtgaat | 420 |
| gagacggctt | ttaccgggcc | ctggggtcgt | ccacagaggg | acggaccagc | gttgagagcg | 480 |
| acggccctca | ttgcgtatgc | gaactatctc | atcgacaacg | gcgaggcttc | gactgccgat | 540 |
| gagatcatct | ggccgattgt | ccagaatgat | ctgtcctaca | tcacccaata | ctggaactca | 600 |
| tccaccttcg | acctctggga | agaagtagaa | ggatcctcat | tcttcacaac | cgccgtgcaa | 660 |
| caccgcgccc | tggtcgaagg | caatgcactg | gcaacaaggc | tgaaccacac | gtgctccaac | 720 |
| tgcgtctctc | aggccgctca | ggtcctgtgt | ttcctgcagt | catactggac | cggatcgtat | 780 |
| gttctggcca | actttggtgg | cagcggtcgt | tccggcaagg | acgtgaattc | gattctgggc | 840 |
| agcatccaca | cctttgatcc | cgccggaggc | tgtgacgact | cgaccttcca | gccgtgttcg | 900 |
| gcccgtgcct | tggcaaatca | caaggtggtc | accgactcgt | tccggagtat | ctatgcgatc | 960 |
| aactcaggca | tcgcagaggg | atctgccgtg | gcagtcggcc | gctacctga | ggatgtctac | 1020 |
| cagggcggga | cccctggta | cctggccaca | gcagcggctg | cagagcagct | ttacgacgcc | 1080 |
| atctaccagt | ggaagaagat | cggctcgata | agtatcacgg | acgttagtct | gccatttttc | 1140 |
| caggatatct | accttctgc | cgcggtgggc | acctataact | ctggctccac | gactttcaac | 1200 |
| gacatcatct | cggccgtcca | gacgtatggt | gatggatatc | tgagtattgt | cgagaaatat | 1260 |
| actccctcag | acggctctct | taccgaacaa | ttctcccgta | cagacggcac | tccgctttct | 1320 |
| gcctctgccc | tgacttggtc | gtacgcttct | ctcctaaccg | cttcggcccg | cagacagtcc | 1380 |
| gtcgtccctg | cttcctgggg | cgaaagctcc | gcaagcagcg | tccctgccgt | ctgctctgcc | 1440 |
| acctctgcca | cgggcccata | cagcacggct | accaacaccg | tctggccaag | ctctggctct | 1500 |
| ggcagctcaa | caaccaccag | tagcgcccca | tgcaccactc | ctacctctgt | ggctgtgacc | 1560 |
| ttcgacgaaa | tcgtcagcac | cagttacggg | gagacaatct | acctggccgg | ctcgatcccc | 1620 |
| gagctgggca | actggtccac | ggccagcgcg | atccccctcc | gcgcggatgc | ttacaccaac | 1680 |
| agcaacccgc | tctggtacgt | gaccgtcaat | ctgcccctg | caccagctt | cgagtacaag | 1740 |
| ttcttcaaga | accagacgga | cgggaccatc | gtctgggaag | acgacccgaa | ccggtcgtac | 1800 |
| acggtcccag | cgtactgtgg | gcagactacc | gccattcttg | acgatagttg | gcagtga | 1857 |

<210> SEQ ID NO 20
<211> LENGTH: 618
<212> TYPE: PRT
<213> ORGANISM: Talaromyces emersonii

<400> SEQUENCE: 20

-continued

```
Met Ala Ser Leu Val Ala Gly Ala Leu Cys Ile Leu Gly Leu Thr Pro
1               5                   10                  15

Ala Ala Phe Ala Arg Ala Pro Val Ala Arg Ala Thr Gly Ser Leu
            20                  25                  30

Asp Ser Phe Leu Ala Thr Glu Thr Pro Ile Ala Leu Gln Gly Val Leu
        35                  40                  45

Asn Asn Ile Gly Pro Asn Gly Ala Asp Val Ala Gly Ala Ser Ala Gly
50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
            100                 105                 110

Ala Gln Ala Lys Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
    130                 135                 140

Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Glu Ala
                165                 170                 175

Ser Thr Ala Asp Glu Ile Ile Trp Pro Ile Val Gln Asn Asp Leu Ser
            180                 185                 190

Tyr Ile Thr Gln Tyr Trp Asn Ser Ser Thr Phe Asp Leu Trp Glu Glu
        195                 200                 205

Val Glu Gly Ser Ser Phe Phe Thr Thr Ala Val Gln His Arg Ala Leu
    210                 215                 220

Val Glu Gly Asn Ala Leu Ala Thr Arg Leu Asn His Thr Cys Ser Asn
225                 230                 235                 240

Cys Val Ser Gln Ala Pro Gln Val Leu Cys Phe Leu Gln Ser Tyr Trp
                245                 250                 255

Thr Gly Ser Tyr Val Leu Ala Asn Phe Gly Gly Ser Gly Arg Ser Gly
            260                 265                 270

Lys Asp Val Asn Ser Ile Leu Gly Ser Ile His Thr Phe Asp Pro Ala
        275                 280                 285

Gly Gly Cys Asp Asp Ser Thr Phe Gln Pro Cys Ser Ala Arg Ala Leu
    290                 295                 300

Ala Asn His Lys Val Val Thr Asp Ser Phe Arg Ser Ile Tyr Ala Ile
305                 310                 315                 320

Asn Ser Gly Ile Ala Glu Gly Ser Ala Val Ala Val Gly Arg Tyr Pro
                325                 330                 335

Glu Asp Val Tyr Gln Gly Gly Asn Pro Trp Tyr Leu Ala Thr Ala Ala
            340                 345                 350

Ala Ala Glu Gln Leu Tyr Asp Ala Ile Tyr Gln Trp Lys Lys Ile Gly
        355                 360                 365

Ser Ile Ser Ile Thr Asp Val Ser Leu Pro Phe Phe Gln Asp Ile Tyr
    370                 375                 380

Pro Ser Ala Ala Val Gly Thr Tyr Asn Ser Gly Ser Thr Thr Phe Asn
385                 390                 395                 400

Asp Ile Ile Ser Ala Val Gln Thr Tyr Gly Asp Gly Tyr Leu Ser Ile
                405                 410                 415

Val Glu Lys Tyr Thr Pro Ser Asp Gly Ser Leu Thr Glu Gln Phe Ser
```

```
                    420               425               430
Arg Thr Asp Gly Thr Pro Leu Ser Ala Ser Ala Leu Thr Trp Ser Tyr
        435               440               445

Ala Ser Leu Leu Thr Ala Ser Ala Arg Arg Gln Ser Val Pro Ala
450             455               460

Ser Trp Gly Glu Ser Ser Ala Ser Ser Val Pro Ala Val Cys Ser Ala
465             470               475               480

Thr Ser Ala Thr Gly Pro Tyr Ser Thr Ala Thr Asn Thr Val Trp Pro
            485               490               495

Ser Ser Gly Ser Gly Ser Ser Thr Thr Thr Ser Ser Ala Pro Cys Thr
            500               505               510

Thr Pro Thr Ser Val Ala Val Thr Phe Asp Glu Ile Val Ser Thr Ser
        515               520               525

Tyr Gly Glu Thr Ile Tyr Leu Ala Gly Ser Ile Pro Glu Leu Gly Asn
    530               535               540

Trp Ser Thr Ala Ser Ala Ile Pro Leu Arg Ala Asp Ala Tyr Thr Asn
545             550               555               560

Ser Asn Pro Leu Trp Tyr Val Thr Val Asn Leu Pro Pro Gly Thr Ser
                565               570               575

Phe Glu Tyr Lys Phe Phe Lys Asn Gln Thr Asp Gly Thr Ile Val Trp
            580               585               590

Glu Asp Asp Pro Asn Arg Ser Tyr Thr Val Pro Ala Tyr Cys Gly Gln
        595               600               605

Thr Thr Ala Ile Leu Asp Asp Ser Trp Gln
    610               615

<210> SEQ ID NO 21
<211> LENGTH: 1725
<212> TYPE: DNA
<213> ORGANISM: Trametes cingulata

<400> SEQUENCE: 21
atgcgtttca cgctcctcac ctccctcctg ggcctcgccc tcggcgcgtt cgcgcagtcg      60
agtgcggccg acgcgtacgt cgcgtccgaa tcgcccatcg ccaaggcggg tgtgctcgcc     120
aacatcgggc ccagcggctc caagtccaac ggagcaaagg caggcatcgt gattgcaagt     180
ccgagcacat ccaacccgaa ctacctgtac acatggacgc gcgactcgtc cctcgtgttc     240
aaggcgctca tcgaccagtt caccactggc gaagatacct cgctccgaac tctgattgac     300
gagttcacct cggcggaggc catactccag caggtgccga acccgagcgg gacagtcagc     360
actggaggcc tcggcgagcc caagttcaac atcgacgaga ccgcgttcac ggatgcctgg     420
ggtcgtcctc agcgcgatgg tcccgctctc cgggcgactg ccatcatcac ctacgccaac     480
tggctcctcg acaacaagaa cacgacctac gtgaccaaca ctctctggcc tatcatcaag     540
ctcgacctcg actacgtcgc cagcaactgg aaccagtcca cgtttgatct ctgggaggag     600
attaactcct cgtcgttctt cactaccgcc gtccagcacc gtgctctgcg cgagggcgcg     660
actttcgcta atcgcatcgg acaaacctcg gtggtcagcg ggtacaccac ccaagcaaac     720
aaccttctct gcttcctgca gtcgtactgg aaccccaccg cggctatat caccgcaaac     780 acgggcggcg gcgctctgg caaggacgcg aacaccgttc tcacgtcgat ccacaccttc     840
gacccggccg ctggatgcga cgctgttacg ttccagccgt gctcggacaa ggcgctgtcg     900
aacttgaagg tgtacgtcga tgcgttccgc tcgatctact ccatcaacag cgggatcgcc     960
tcgaatgcgg ccgttgctac cggccgctac cccgaggaca gctacatggg cggaaaccca    1020
```

```
tggtacctca ccacctccgc cgtcgctgag cagctctacg atgcgctcat tgtgtggaac    1080
aaacttggcg ccctgaacgt cacgagcacc tccctccccct tcttccagca gttctcgtca    1140
ggcgtcaccg tcggcaccta tgcctcatcc tcgtccacct tcaagacgct cacttccgcc    1200
atcaagacct tcgccgacgg cttcctcgcg gtcaacgcca agtacacgcc ctcgaacggc    1260
ggccttgctg aacagtacag ccggagcaac ggctcgcccg tcagcgctgt ggacctgacg    1320
tggagctatg ctgctgccct cacgtcgttt gctgcgcgct caggcaagac gtatgcgagc    1380
tggggcgcgg cgggtttgac tgtcccgacg acttgctcgg ggagtggcgg tgctgggact    1440
gtggccgtca ccttcaacgt gcaggcgacc accgtgttcg gcgagaacat ttacatcaca    1500
ggctcggtcc ccgctctcca gaactggtcg cccgacaacg cgctcatcct ctcagcggcc    1560
aactacccca cttggagcat caccgtgaac ctgccggcga gcacgacgat cgagtacaag    1620
tacattcgca agttcaacgg cgcggtcacc tgggagtccg acccgaacaa ctcgatcacg    1680
acgcccgcga gcggcacgtt cacccagaac gacacctggc ggtag              1725
```

<210> SEQ ID NO 22
<211> LENGTH: 574
<212> TYPE: PRT
<213> ORGANISM: Trametes cingulata

<400> SEQUENCE: 22

```
Met Arg Phe Thr Leu Leu Thr Ser Leu Leu Gly Leu Ala Leu Gly Ala
1               5                   10                  15

Phe Ala Gln Ser Ser Ala Ala Asp Ala Tyr Val Ala Ser Glu Ser Pro
            20                  25                  30

Ile Ala Lys Ala Gly Val Leu Ala Asn Ile Gly Pro Ser Gly Ser Lys
        35                  40                  45

Ser Asn Gly Ala Lys Ala Gly Ile Val Ile Ala Ser Pro Ser Thr Ser
    50                  55                  60

Asn Pro Asn Tyr Leu Tyr Thr Trp Thr Arg Asp Ser Ser Leu Val Phe
65                  70                  75                  80

Lys Ala Leu Ile Asp Gln Phe Thr Thr Gly Glu Asp Thr Ser Leu Arg
                85                  90                  95

Thr Leu Ile Asp Glu Phe Thr Ser Ala Glu Ala Ile Leu Gln Gln Val
            100                 105                 110

Pro Asn Pro Ser Gly Thr Val Ser Thr Gly Gly Leu Gly Glu Pro Lys
        115                 120                 125

Phe Asn Ile Asp Glu Thr Ala Phe Thr Asp Ala Trp Gly Arg Pro Gln
    130                 135                 140

Arg Asp Gly Pro Ala Leu Arg Ala Thr Ala Ile Ile Thr Tyr Ala Asn
145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
            180                 185                 190

Ser Thr Phe Asp Leu Trp Glu Glu Ile Asn Ser Ser Phe Phe Thr
        195                 200                 205

Thr Ala Val Gln His Arg Ala Leu Arg Glu Gly Ala Thr Phe Ala Asn
    210                 215                 220
```

-continued

```
Arg Ile Gly Gln Thr Ser Val Val Ser Gly Tyr Thr Thr Gln Ala Asn
225                 230                 235                 240

Asn Leu Leu Cys Phe Leu Gln Ser Tyr Trp Asn Pro Thr Gly Gly Tyr
            245                 250                 255

Ile Thr Ala Asn Thr Gly Gly Arg Ser Gly Lys Asp Ala Asn Thr
            260                 265                 270

Val Leu Thr Ser Ile His Thr Phe Asp Pro Ala Ala Gly Cys Asp Ala
            275                 280                 285

Val Thr Phe Gln Pro Cys Ser Asp Lys Ala Leu Ser Asn Leu Lys Val
        290                 295                 300

Tyr Val Asp Ala Phe Arg Ser Ile Tyr Ser Ile Asn Ser Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Ile Val Trp Asn Lys Leu Gly Ala Leu Asn Val Thr
        355                 360                 365

Ser Thr Ser Leu Pro Phe Phe Gln Gln Phe Ser Ser Gly Val Thr Val
370                 375                 380

Gly Thr Tyr Ala Ser Ser Ser Ser Thr Phe Lys Thr Leu Thr Ser Ala
385                 390                 395                 400

Ile Lys Thr Phe Ala Asp Gly Phe Leu Ala Val Asn Ala Lys Tyr Thr
            405                 410                 415

Pro Ser Asn Gly Gly Leu Ala Glu Gln Tyr Ser Arg Ser Asn Gly Ser
            420                 425                 430

Pro Val Ser Ala Val Asp Leu Thr Trp Ser Tyr Ala Ala Ala Leu Thr
            435                 440                 445

Ser Phe Ala Ala Arg Ser Gly Lys Thr Tyr Ala Ser Trp Gly Ala Ala
450                 455                 460

Gly Leu Thr Val Pro Thr Thr Cys Ser Gly Ser Gly Ala Gly Thr
465                 470                 475                 480

Val Ala Val Thr Phe Asn Val Gln Ala Thr Thr Val Phe Gly Glu Asn
            485                 490                 495

Ile Tyr Ile Thr Gly Ser Val Pro Ala Leu Gln Asn Trp Ser Pro Asp
            500                 505                 510

Asn Ala Leu Ile Leu Ser Ala Ala Asn Tyr Pro Thr Trp Ser Ile Thr
            515                 520                 525

Val Asn Leu Pro Ala Ser Thr Thr Ile Glu Tyr Lys Tyr Ile Arg Lys
530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
            565                 570
```

US 9,102,928 B2

POLYPEPTIDES HAVING GLUCOAMYLASE ACTIVITY AND POLYNUCLEOTIDES ENCODING SAME

CROSS-REFERENCE TO RELATED APPLICATIONS

This application is a continuation of U.S. application Ser. No. 13/500,325 filed May 3, 2012 (now U.S. Pat. No. 8,557, 541), which is a 35 U.S.C. 371 national application of PCT/US2010/058424 filed Nov. 30, 2010, which claims priority or the benefit under 35 U.S.C. 119 of U.S. provisional application nos. 61/265,526 and 61/406,741 filed Dec. 1, 2009 and Oct. 26, 2010, respectively, the contents of which are fully incorporated herein by reference.

REFERENCE TO A DEPOSIT OF BIOLOGICAL MATERIAL

This application contains a Sequence Listing in computer readable form, which is incorporated herein by reference.

REFERENCE TO A DEPOSIT OF BIOLOGICAL MATERIAL

This application contains a reference to a deposit of biological material, which deposit is incorporated herein by reference. For complete information see last paragraph of the description.

BACKGROUND OF THE INVENTION

1. Field of the Invention

The present invention relates to polypeptides having glucoamylase activity and polynucleotides encoding the polypeptides. The invention also relates to nucleic acid constructs, vectors, and host cells comprising the polynucleotides as well as methods for producing and using the polypeptides, and to the use of glucoamylases of the invention for starch conversion to producing fermentation products, such as ethanol, and syrups, such as glucose. The invention also relates to a composition comprising a glucoamylase of the invention.

2. Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starchy material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be a syrup. For instance, the end product may be glucose, but may also be converted, e.g., by a glucose isomerase to fructose or a mixture composed almost equally of glucose and fructose. This mixture, or a mixture further enriched with fructose, is the most commonly used high fructose corn syrup (HFCS) commercialized throughout the world.

It is an object of the present invention to provide polypeptides having glucoamylase activity and polynucleotides encoding the polypeptides and which provide a high yield in fermentation product production processes, such as ethanol production processes, including one-step ethanol fermentation processes from un-gelatinized raw (or uncooked) starch.

Uniprot: B0CVJ1 discloses a polypeptide from *Laccaria bicolor* and WO 2006/069289 describes a glucoamylase from *Trametes cingulata*.

SUMMARY OF THE INVENTION

Polypeptides produced by the fungus *Gloeophyllum* and having glucoamylase activity have been identified and characterized. More particularly the *Gloeophillum* sp. is selected from the group consisting of *G. abietinum, G. sepiarium*, and *G. trabeum*.

Accordingly, the present invention relates in a first aspect to an isolated polypeptide having glucoamylase activity, selected from the group consisting of: (a) a polypeptide comprising an amino acid sequence having preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, even more preferably at least 93%, most preferably at least 94%, and even most preferably at least 95%, such as at least 96%, at least 97%, at least 98%, at least 99% or even 100% identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18; (b) a polypeptide comprising an amino acid sequence having preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, even more preferably at least 93%, most preferably at least 94%, and even most preferably at least 95%, such as at least 96%, at least 97%, at least 98%, at least 99% or even 100% identity to the catalytic domain shown as amino acids 19 to 474 of SEQ ID NO: 2, SEQ ID NO: 4, SEQ ID NO: 6, SEQ ID NO: 8, SEQ ID NO: 10, SEQ ID NO: 12, SEQ ID NO: 14 or amino acids 19 to 471 of SEQ ID NO: 16 or of SEQ ID NO: 18; c) a polypeptide encoded by a polynucleotide that hybridizes under preferably at least medium-high stringency conditions, and most preferably at least high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, (ii) the genomic DNA sequence comprising the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, or (iii) a full-length complementary strand of (i) or (ii); (d) a polypeptide encoded by a polynucleotide comprising a nucleotide sequence having preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, even more preferably at least 93%, most preferably at least 94%, and even most preferably at least 95%, such as at least 96%, at least 97%, at least 98%, at least 99% or even 100% identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17; and (e) a variant comprising a substitution, deletion, and/or insertion of one or more (several) amino acids of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

The present invention relates in a second aspect to an isolated polynucleotide comprising a nucleotide sequence that encodes the polypeptide of the first aspect.

In further aspects the invention relates to a nucleic acid construct, a recombinant expression vector, a recombinant host cell, a transgenic plant, a plant part or plant cell comprising the polynucleotide of the second aspect.

In still further aspects the invention relates to a method of producing the polypeptide, uses of the polypeptide and a composition comprising an alpha-amylase and the polypeptide.

DEFINITIONS

Glucoamylase: The term glucoamylase (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the 'Materials & Methods'-section below.

The polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 2 or a homologous sequence thereof, SEQ ID NO: 4 or a homologous sequence thereof, SEQ ID NO: 6 or a homologous sequence thereof, SEQ ID NO: 8 or a homologous sequence thereof, SEQ ID NO: 10 or a homologous sequence thereof, SEQ ID NO: 12 or a homologous sequence thereof, SEQ ID NO: 14 or a homologous sequence thereof, SEQ ID NO: 16 or a homologous sequence thereof, or SEQ ID NO: 18 or a homologous sequence thereof.

Isolated polypeptide: The term "isolated polypeptide" as used herein refers to a polypeptide that is isolated from a source. Preferably, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 18 to 573 of SEQ ID NO: 2, SEQ ID NO: 4, SEQ ID NO: 6, SEQ ID NO: 8, SEQ ID NO: 10, SEQ ID NO: 12, SEQ ID NO: 14 or amino acids 18 to 576 of SEQ ID NO: 16, or of SEQ ID NO: 18 based on the SignalP program (Nielsen et al., 1997, *Protein Engineering* 10: 1-6) that predicts amino acids 1 to 17 of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16 and SEQ ID NO: 18 are a signal peptide. The sequence defined by amino acids 19 to 474 (particularly 19 to 471) of SEQ ID NO: 2, SEQ ID NO: 4, SEQ ID NO: 6, SEQ ID NO: 8, SEQ ID NO: 10, SEQ ID NO: 12, or SEQ ID NO: 14 or amino acids 19 to 471 of SEQ ID NO: 16 or of SEQ ID NO: 18 is the catalytic domain. The sequence defined by amino acids 480 to 573 of SEQ ID NO: 2, SEQ ID NO: 4, SEQ ID NO: 6, SEQ ID NO: 8, SEQ ID NO: 10, SEQ ID NO: 12, or SEQ ID NO: 14 or amino acids 483 to 576 of SEQ ID NO: 16 or SEQ ID NO: 18 is a starch binding domain.

Mature polypeptide coding sequence: The term "mature polypeptide coding sequence" is defined herein as a nucleotide sequence that encodes a mature polypeptide having glucoamylase activity. Preferably, the mature polypeptide coding sequence is nucleotides 52 to 1719 of SEQ ID NO: 1, SEQ ID NO: 3, SEQ ID NO: 5, SEQ ID NO: 7, SEQ ID NO: 9, SEQ ID NO: 11, SEQ ID NO: 13, or nucleotides 52 to 1728 of SEQ ID NO: 15 or of SEQ ID NO: 17.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Homologous sequence: The term "homologous sequence" is defined herein as a nucleotide sequence/polypeptide sequence having a % identity to the mature polypeptide encoding part of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 or to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, respectively, of at least 82%, preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, even more preferably at least 93%, most preferably at least 94%, and even most preferably at least 95%, such as at least 96%, at least 97%, at least 98%, or even at least 99%.

Polypeptide fragment: The term "polypeptide fragment" is defined herein as a polypeptide having one or more (several) amino acids deleted from the amino and/or carboxyl terminus of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18; or a homologous sequence thereof; wherein the fragment has glucoamylase activity. Preferably, a fragment contains at least 500 amino acid residues, more preferably at least 450 amino acid, and most preferably at least 400 amino acid residues, of the mature polypeptide of SEQ ID NO: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, or a homologous sequence thereof. A particular fragment is the sequence defined by amino acids 19 to 474 of SEQ ID NO: 2, SEQ ID NO: 4, SEQ ID NO: 6, SEQ ID NO: 8, SEQ ID NO: 10, SEQ ID NO: 12, or SEQ ID NO: 14 or amino acids 19 to 471 of SEQ ID NO: 16 or of SEQ ID NO: 18 which comprises the catalytic domain of the polypeptide of the invention.

Subsequence: The term "subsequence" is defined herein as a nucleotide sequence having one or more (several) nucleotides deleted from the 5' and/or 3' end of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17; or a homologous sequence thereof; wherein the subsequence encodes a polypeptide fragment having glucoamylase activity. Preferably, a subsequence contains at least 1500 nucleotides, more preferably at least 1400 nucleotides, and most preferably at least 1200 nucleotides of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. Preferably, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Variant: When used herein, the term "variant" means a polypeptide having glucoamylase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

DETAILED DESCRIPTION OF THE INVENTION

Polypeptides Having Glucoamylase Activity

In a first aspect, the present invention relates to isolated polypeptides comprising an amino acid sequence having a degree of identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 of preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, even more preferably at least 93%, most preferably at least 94%, and even most preferably at least 95%, such as at least 96%, at least 97%, at least 98%, at least 99% or even 100% identity, which have glucoamylase activity (hereinafter "homologous polypeptides"). Preferably, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

A polypeptide of the present invention preferably comprises the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 or an allelic variant thereof; or a fragment thereof having glucoamylase activity. Preferably, the polypeptide comprises the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18. In another preferred aspect, the polypeptide comprises the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 or an allelic variant thereof; or a fragment thereof having glucoamylase activity. In another preferred aspect, the polypeptide consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 or an allelic variant thereof; or a fragment thereof having glucoamylase activity. In another preferred aspect, the polypeptide consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

In a second aspect, the present invention relates to isolated polypeptides having glucoamylase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, (ii) the genomic DNA sequence comprising the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 contains at least 100 contiguous nucleotides or preferably at least 200 contiguous nucleotides. Moreover, the subsequence may encode a polypeptide fragment having glucoamylase activity. Preferably, the complementary strand is the full-length complementary strand of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17.

The nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17; or a subsequence thereof; as well as the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18; or a fragment thereof; may be used to design nucleic acid probes to identify and clone DNA encoding polypeptides having glucoamylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{33}P$, $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having glucoamylase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17; the genomic DNA sequence comprising the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17; its full-length complementary strand; or a subsequence thereof; under very low to very high stringency conditions. Molecules to which the nucleic acid probe hybridizes under these conditions can be detected using, for example, X-ray film.

Preferably, the nucleic acid probe is the mature polypeptide coding sequence of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid in *E. coli* strain DSM 23222, wherein the polynucleotide sequence thereof encodes a polypeptide having glucoamylase activity. In another preferred aspect, the nucleic acid probe is the mature polypeptide coding region contained in plasmid in *E. coli* strain DSM 23222.

Preferably, the nucleic acid probe is the mature polypeptide coding sequence of SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17. In another preferred aspect, the nucleic acid probe is a polynucleotide sequence that encodes the polypeptide of SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, or a subsequence thereof. In another preferred aspect, the nucleic acid probe is SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having glucoamylase activity encoded by polynucleotides comprising or consisting of nucleotide sequences that have a degree of identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 of at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, even more preferably at least 93%, most preferably at least 94%, and even most preferably at least 95%, such as at least 96%, at least 97%, at least 98%, at least 99%, which encode an active polypeptide. See polynucleotide section herein.

The present invention also relates to artificial variants comprising a substitution, deletion, and/or insertion of one or more (or several) amino acids of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30: 10832-10837; U.S. Pat. No. 5,223, 409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide, such as amino acids 18 to 573 of SEQ ID NO: 2, SEQ ID NO: 4, SEQ ID NO: 6, SEQ ID NO: 8, SEQ ID NO: 10, SEQ ID NO: 12, or SEQ ID NO: 14 or amino acids 18 to 576 of SEQ ID NO: 16 or SEQ ID NO: 18, or the catalytic domain, such as amino acids 19 to 474 of SEQ ID NO: 2, SEQ ID NO: 4, SEQ ID NO: 6, SEQ ID NO: 8, SEQ ID NO: 10, SEQ ID NO: 12, or SEQ ID NO: 14 or amino acids 19 to 471 of SEQ ID NO: 16 or of SEQ ID NO: 18, is 10, preferably 9, more preferably 8, more preferably 7, more preferably at most 6, more preferably 5, more preferably 4, even more preferably 3, most preferably 2, and even most preferably 1.

Sources of Polypeptides Having Glucoamylase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. Preferably, the polypeptide obtained from a given source is secreted extracellularly.

A polypeptide having glucoamylase activity of the present invention may also be bacterial polypeptide, or a yeast polypeptide, or more preferably a filamentous fungal polypeptide such as an *Acremonium*, *Agaricus*, *Alternaria*, *Artomyces*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Gloeophyllum*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having glucoamylase activity.

In a more preferred aspect, the polypeptide is a *Gloeophyllum* sp. polypeptide, such as a *Gloeophyllum sepiarium*, *Gloeophyllum trabeum*, or *Gloeophyllum abietinum* polypeptide having glucoamylase activity. It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having glucoamylase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); an Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having glucoamylase activity of the present invention.

Preferably, the nucleotide sequence comprises or consists of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17. In another preferred aspect, the nucleotide sequence comprises or consists of the sequence contained in plasmid which is contained in *E. coli* DSM 23222. In another preferred aspect, the nucleotide sequence comprises or consists of the mature polypeptide coding sequence of SEQ ID NO: 1. In another more preferred aspect, the nucleotide sequence comprises or consists of the mature polypeptide coding sequence contained in plasmid contained in *E. coli* DSM 23222. The present invention also encompasses nucleotide sequences that encode polypeptides comprising or consisting of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 or the mature polypeptides thereof, which differ from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 or the mature polypeptide coding sequence thereof by virtue of the degeneracy of the genetic code. The present invention also relates to subsequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 that encodes fragments of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 that have glucoamylase activity.

The present invention also relates to mutant polynucleotides comprising or consisting of at least one mutation in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, in which the mutant nucleotide sequence encodes the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Penicillium*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17 of preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, even more preferably at least 93%, most preferably at least 94%, and even most preferably at least 95%, such as at least 96%, at least 97%, at least 98%, at least 99% or even 100% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for glucoamylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, (ii) the genomic DNA sequence comprising the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, or (iii) a full-length complementary strand of (i) or (ii); or allelic variants and subsequences thereof (Sambrook et al., 1989, supra), as defined herein. Preferably, the complementary strand is the full-length complementary strand of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, (ii) the genomic DNA sequence comprising the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, or (iii) a full-length complementary strand of (i) or (ii); and (b) isolating the hybridizing polynucleotide, which encodes a polypeptide having glucoamylase activity. Preferably, the complementary strand is the full-length complementary strand of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17.

Hybrid Enzymes

The present invention also relates to hybrid enzymes comprising a catalytic domain having enzyme activity (e.g., starch degrading enzyme activity, such as alpha-amylase, amylopullulanase, beta-amylase, CGTase, glucoamylase, isoamylase, maltogenic amylase, or pullulanase activity), and a carbohydrate-binding module (CBM). The hybrid enzyme may further comprise a linker.

The hybrid may be produced by fusing a first DNA sequence encoding a catalytic domain and a second DNA sequence encoding a carbohydrate-binding module, or the hybrid may be produced as a completely synthetic gene based on knowledge of the amino acid sequences of suitable CBMs, linkers and catalytic domains.

The term "hybrid enzyme" (also referred to as "fusion protein", "hybrid", hybrid polypeptide" or "hybrid protein") is used herein to characterize the hybrid polypeptides of the invention comprising a catalytic module having enzyme activity (e.g., starch degrading enzyme activity, such as alpha-amylase, amylopullulanase, beta-amylase, CGTase, glucoamylase, isoamylase, maltogenic amylase, or pullulanase activity) and a carbohydrate-binding module wherein the catalytic domain and the carbohydrate-binding module are derived from different sources. The term "source" includes, but is not limited to, a parent enzyme or a variant thereof, e.g., an amylase or glucoamylase, or other catalytic activity comprising a suitable catalytic module and/or a suitable CBM and/or a suitable linker. However the CBM may also be derived from a polypeptide having no catalytic activity. The catalytic domain and the carbohydrate binding module may be derived from the same microbial strain, from strains within the same species, from closely related species or less related organisms. Preferably the catalytic domain and the carbohydrate binding module of the hybrids are derived from different sources, e.g., from different enzymes from the same strain and/or species, or e.g., from strains within different species.

In one aspect the hybrid enzyme comprises the CBM (also known as a carbohydrate binding domain or CBD) according to the invention and a catalytic domain. The catalytic domain is in a particular embodiment a glucoamylase catalytic domain.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus niger* neutral alpha-amylase, *Aspergillus niger* acid stable alpha-amylase, *Aspergillus oryzae* TAKA amylase, *Aspergillus awamori* or *Aspergillus niger* glucoamylase (glaA), *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Rhizomucor miehei* aspartic proteinase, *Rhizomucor miehei* lipase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus nidulans* anthranilate synthase, *Aspergillus niger* alpha-glucosidase, *Aspergillus niger* glucoamylase, *Aspergillus oryzae* TAKA amylase, and *Fusarium oxysporum* trypsin-like protease.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, xyl and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive bacterium or gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *E. coli, Campylobacter, Flavobacterium, Fusobacterium, Helicobacter, Ilyobacter, Neisseria, Pseudomonas, Salmonella*, and *Ureaplasma*.

The host cell may also be a eukaryote, such as a mammalian, insect, plant, or fungal cell.

Preferably, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus foetidus, Aspergillus fumigatus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes versicolor, Trametes villosa, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 0238023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology* 194: 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. Preferably, the cell is of the genus *Gloeophyllum*. In a more preferred aspect, the cell is of the species *Gloeophyllum sepiarium, Gloeophyllum trabeum*, or *Gloeophyllum abietinum*.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, wherein the mutant nucleotide sequence encodes a polypeptide that comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having glucoamylase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mol. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having glucoamylase activity of the present invention under conditions conducive for production of the polypeptide; and (b) recovering the polypeptide.

Compositions

The present invention also relates to compositions comprising a polypeptide of the present invention. Preferably, the compositions are enriched in such a polypeptide. The term "enriched" indicates that the glucoamylase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulaturn*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiaturn*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Combination of Glucoamylase and Acid Alpha-Amylase

According to this aspect of the invention a glucoamylase of the invention may be combined with an alpha-amylase, preferably acid alpha-amylase in a ratio of between 0.3 and 5.0 AFAU/AGU. More preferably the ratio between acid alpha-amylase activity and glucoamylase activity is at least 0.35, at least 0.40, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.85, or even at least 1.9 AFAU/AGU. However, the ratio between acid alpha-amylase activity and glucoamylase activity should preferably be less than 4.5, less than 4.0, less than 3.5, less than 3.0, less than 2.5, or even less than 2.25 AFAU/AGU. In AUU/AGI the activities of acid alpha-amylase and glucoamylase are preferably present in a ratio of between 0.4 and 6.5 AUU/AGI. More preferably the ratio between acid alpha-amylase activity and glucoamylase activity is at least 0.45, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, or even at least 2.5 AUU/AGI. However, the ratio between acid alpha-amylase activity and glucoamylase activity is preferably less than 6.0, less than 5.5, less than 4.5, less than 4.0, less than 3.5, or even less than 3.0 AUU/AGI.

Above composition is suitable for use in a starch conversion process mentioned below for producing syrup and fermentation products, such as ethanol.

Examples are given below of preferred uses of the polypeptide compositions of the invention. The dosage of the polypeptide composition of the invention and other conditions under which the composition is used may be determined on the basis of methods known in the art.

Uses

The present invention is also directed to processes/methods for using the polypeptides having glucoamylase activity of the invention.

Uses according to the invention include starch conversion of starch to, e.g., syrup and fermentation products, including ethanol and beverages. Examples of processes where a glucoamylase of the invention may be used include the ones described in WO 92/20777, WO 03/066816, WO 03/066826, WO 2004/080923, and WO 2004/081193, which are hereby all incorporated by reference.

Production of Fermentation Products

Process for Producing Fermentation Products from Gelatinized Starch Containing Material In this aspect the present invention relates to a process for producing a fermentation product, especially ethanol, from starch-containing material, which process includes a liquefaction step and sequentially or simultaneously performed saccharification and fermentation steps.

The invention relates to a process for producing a fermentation product from starch-containing material comprising the steps of:

(a) liquefying starch-containing material; preferably using an alpha-amylase (b) saccharifying the liquefied material obtained in step (a) using a glucoamylase of the invention; and (c) fermenting the saccharified material using a fermenting organism.

The fermentation product, such as especially ethanol, may optionally be recovered after fermentation, e.g., by distillation. Suitable starch-containing starting materials are listed in the section "Starch-containing materials"-section below. Contemplated enzymes are listed in the "Enzymes"-section below. The liquefaction is preferably carried out in the presence of an alpha-amylase. The fermentation is preferably carried out in the presence of yeast, preferably a strain of *Saccharomyces*. Suitable fermenting organisms are listed in the "Fermenting Organisms"-section below. In preferred embodiments step (b) and (c) are carried out sequentially or simultaneously (i.e., as SSF process).

In a particular embodiment, the process of the invention further comprises, prior to the step (a), the steps of:

x) reducing the particle size of the starch-containing material, preferably by milling; and y) forming a slurry comprising the starch-containing material and water.

The aqueous slurry may contain from 10-40 wt. %, preferably 25-35 wt. % starch-containing material. The slurry is heated to above the gelatinization temperature and alpha-amylase, preferably bacterial and/or acid fungal alpha-amylase, may be added to initiate liquefaction (thinning). The slurry may in an embodiment be jet-cooked to further gelatinize the slurry before being subjected to an alpha-amylase in step (a) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for 1-15 minutes, preferably for 3-10 minute, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (b) may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 30-65° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s) may be added together. SSF may typically be carried out at a temperature between 25° C. and 40° C., such as between 29° C. and 35° C., such as between 30° C. and 34° C., such as around 32° C. According to the invention the temperature may be adjusted up or down during fermentation.

In accordance with the present invention the fermentation step (c) includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. Preferred fermentation processes include alcohol fermentation processes, as are well known in the art. Preferred fermentation processes are anaerobic fermentation processes, as are well known in the art.

Processes for Producing Fermentation Products from Un-Gelatinized Starch-Containing In this aspect the invention relates to processes for producing a fermentation product from starch-containing material without gelatinization of the starch-containing material (i.e., uncooked starch-containing material). In one embodiment only a glucoamylase of the invention is used during saccharification and fermentation. According to the invention the desired fermentation product, such as ethanol, can be produced without liquefying the aqueous slurry containing the starch-containing material. In one embodiment a process of the invention includes saccharifying (milled) starch-containing material, e.g., granular starch, below the gelatinization temperature in the presence of a glucoamylase of the invention to produce sugars that can be fermented into the desired fermentation product by a suitable fermenting organism.

Accordingly, in this aspect the invention relates to a process for producing a fermentation product from starch-containing material comprising:

(a) saccharifying starch-containing material with a mature glucoamylase according to the invention, preferably having the sequence shown as amino acids 18 to 573 of SEQ ID NO: 2, SEQ ID NO: 4, SEQ ID NO: 6, SEQ ID NO: 8, SEQ ID NO: 10, SEQ ID NO: 12, or SEQ ID NO: 14 or amino acids 18 to 576 of SEQ ID NO: 16 or SEQ ID NO: 18, or a glucoamylase having at least 82% identity thereto, at a temperature below the initial gelatinization temperature of said starch-containing material, (b) fermenting using a fermenting organism.

Steps (a) and (b) of the process of the invention may be carried out sequentially or simultaneously. In an embodiment a slurry comprising water and starch-containing material is prepared before step (a).

The fermentation process may be carried out for a period of 1 to 250 hours, preferably is from 25 to 190 hours, more preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein and Lii, 1992, *Starch/Stärke* 44(12): 461-466 (1992).

Before step (a) a slurry of starch-containing material, such as granular starch, having 10-55 wt. % dry solids, preferably 25-40 wt. % dry solids, more preferably 30-35 wt. % dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place, high levels of stillage may be used if desired. In an embodiment the aqueous slurry contains from about 1 to about 70 vol. % stillage, preferably 15-60% vol. % stillage, especially from about 30 to 50 vol. % stillage.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment step (a) and step (b) are carried out as a sequential or simultaneous saccharification and fermentation process. In such preferred embodiment the process is typically carried at a temperature between 25° C. and 40° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low level such as below 6 wt. %, preferably below about 3 wt. %, preferably below about 2 wt. %, more preferred below about 1 wt. %., even more preferred below about 0.5 wt. %, or even more preferred 0.25% wt. %, such as below about 0.1 wt. %. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt. % or below about 0.2 wt. %.

The process of the invention may be carried out at a pH in the range between 3 and 7, preferably from pH 3.5 to 6, or more preferably from pH 4 to 5.

Starch-Containing Materials

Any suitable starch-containing starting material, including granular starch, may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, milo, sago, cassava, tapioca, sorghum, rice, peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch containing material comprising milled whole grain including non-starch fractions such as germ residues and fibers. The raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolysate is used in production of syrups. Both dry and wet milling is well known in the art of starch processing and is equally contemplated for the process of the invention.

The starch-containing material is reduced in particle size, preferably by dry or wet milling, in order to expose more surface area. In an embodiment the particle size is between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, as are well known in the art. Preferred fermentation processes are anaerobic fermentation processes, as are well known in the art.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of *Saccharomyces* spp., in particular, *Saccharomyces cerevisiae*. Commercially available yeast include, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Enzymes

Glucoamylase

The glucoamylase is preferably a glucoamylase of the invention. However, as mentioned above a glucoamylase of the invention may also be combined with other glucoamylases. The term "glucoamylase" (1,4-alpha-D-glucan glucohydrolase, EC 3.2.1.3) is an enzyme, which catalyzes the release of D-glucose from the non-reducing ends of starch or related oligo- and polysaccharide molecules.

The glucoamylase may added in an amount of 0.001 to 10 AGU/g DS, preferably from 0.01 to 5 AGU/g DS, such as around 0.1, 0.3, 0.5, 1 or 2 AGU/g DS, especially 0.1 to 0.5 AGU/g DS or 0.02-20 AGU/g DS, preferably 0.1-10 AGU/g DS.

Alpha-Amylase

The alpha-amylase may according to the invention be of any origin. Preferred are alpha-amylases of fungal or bacterial origin.

In a preferred embodiment the alpha-amylase is an acid alpha-amylase, e.g., fungal acid alpha-amylase or bacterial acid alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase may preferably be derived from the genus *Bacillus*.

In a preferred embodiment the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NO: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,187,576, and 6,297,038 (hereby incorporated by reference) and include *Bacillus stearothermophilus* alpha-amylase (BSG alpha-amylase) variants having a deletion of one or two amino acid in position 179 to 182, preferably a double deletion disclosed in WO 96/23873—see, e.g., page 20, lines 1-10 (hereby incorporated by reference), preferably corresponding to delta(181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181*+G182*+N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, EC 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 4 in WO 99/19467) and the 37 N-terminal amino acid residues of the alpha-amylase derived from *Bacillus amyloliquefaciens* (shown as SEQ ID NO: 3 in WO 99/19467), with one or more, especially all, of the following substitutions:
G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

The bacterial alpha-amylase may be added in amounts as are well-known in the art. When measured in KNU units (described below in the "Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal acid alpha-amylases include acid alpha-amylases derived from a strain of the genus *Aspergillus*, such as *Aspergillus kawachii*, *Aspergillus niger*, or *Aspergillus oryzae* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e., more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

In a preferred embodiment the alpha-amylase is derived from *Aspergillus kawachii* and disclosed by Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL:#AB008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of *Aspergillus kawachii*.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Application Publication no. 2005/0054071 (Novozymes) or U.S. application no. 60/638,614 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include those disclosed in U.S. application No. 60/638,614 including Fungamyl variant with catalytic domain JA118 and *Athelia rolfsii* SBD (SEQ ID NO: 100 in U.S. application no. 60/638,614), *Rhizomucor pusillus* alpha-amylase with *Athelia rolfsii* AMG linker and SBD (SEQ ID NO: 101 in U.S. application no. 60/638,614) and *Meripilus giganteus* alpha-amylase with *Athelia rolfsii* glucoamylase linker and SBD (SEQ ID NO: 102 in U.S. application no. 60/638,614).

Other specific examples of contemplated hybrid alpha-amylases include those disclosed in U.S. Application Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, SPEZYME™ Ethyl, GC358, GC980, SPEZYME™ RSL, and SPEZYME™ DELTA AA (Genencor Int.), and the acid fungal alpha-amylase sold under the trade name SP288 (available from Novozymes NS, Denmark).

An acid alpha-amylase may according to the invention be added in an amount of 0.1 to 10 AFAU/g DS, preferably 0.10 to 5 AFAU/g DS, especially 0.3 to 2 AFAU/g DS.

Production of Syrup

The present invention also provides a process of using a glucoamylase of the invention for producing syrup, such as glucose and the like, from starch-containing material. Suitable starting materials are exemplified in the "Starch-containing materials"-section above. Generally, the process comprises the steps of partially hydrolyzing starch-containing material (liquefaction) in the presence of alpha-amylase and then further saccharifying the release of glucose from the non-reducing ends of the starch or related oligo- and polysaccharide molecules in the presence of glucoamylase of the invention.

Liquefaction and saccharification may be carried our as described above for fermentation product production.

The glucoamylase of the invention may also be used in immobilized form. This is suitable and often used for producing speciality syrups, such as maltose syrups, and further for the raffinate stream of oligosaccharides in connection with the production of fructose syrups, e.g., high fructose syrup (HFS).

Consequently, this aspect of the invention relates to a process of producing syrup from starch-containing material, comprising (a) liquefying starch-containing material in the presence of an alpha-amylase, and (b) saccharifying the material obtained in step (a) using a glucoamylase of the invention.

A syrup may be recovered from the saccharified material obtained in step (b).

Details on suitable conditions can be found above.

Brewing

A glucoamylase of the invention can also be used in a brewing process. The glucoamylase of the invention is added in effective amounts which can be easily determined by the skilled person in the art.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties. The present invention is further described by the following examples which should not be construed as limiting the scope of the invention.

Materials & Methods

Yeast: RED START™ available from Red Star/Lesaffre, USA

Media and Reagents:

Chemicals used as buffers and substrates were commercial products of at least reagent grade.

PDA: 39 g/L Potato Dextrose Agar, 20 g/L agar, 50 ml/L glycerol

Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995;

Harwood, C. R., and Cutting, S. M. (eds.) "Molecular Biological Methods for Bacillus". John Wiley and Sons, 1990.

Glucoamylase Activity

Glucoamylase activity may be measured in AGI units or in Glucoamylase Units (AGU).

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch—Glucoamylase Method with Subsequent Measurement of Glucose with Glucose Oxidase in "Approved methods of the American Association of Cereal Chemists". Vol. 1-2 AACC, from American Association of Cereal Chemists, (2000); ISBN: 1-891127-12-8.

One glucoamylase unit (AGI) is the quantity of enzyme which will form 1 micro mole of glucose per minute under the standard conditions of the method.

Standard Conditions/Reaction Conditions:

Substrate: Soluble starch, concentration approx. 16 g dry matter/L.
Buffer: Acetate, approx. 0.04 M, pH=4.3
pH: 4.3
Incubation temperature: 60° C.
Reaction time: 15 minutes
Termination of the reaction: NaOH to a concentration of approximately 0.2 g/L (pH~9)
Enzyme concentration: 0.15-0.55 AAU/mL.

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

Alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Acid Alpha-Amylase Activity

When used according to the present invention the activity of any acid alpha-amylase may be measured in AFAU (Acid Fungal Alpha-amylase Units). Alternatively activity of acid alpha-amylase may be measured in AAU (Acid Alpha-amylase Units).

Acid Alpha-Amylase Units (AAU)

Acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard Conditions/Reaction Conditions:

Substrate: Soluble starch. Concentration approx. 20 g DS/L.
Buffer: Citrate, approx. 0.13 M, pH=4.2
Iodine solution: 40.176 g potassium iodide+0.088 g iodine/L
City water: 15°-20° dH (German degree hardness)
pH: 4.2
Incubation temperature: 30° C.
Reaction time: 11 minutes
Wavelength: 620 nm
Enzyme concentration: 0.13-0.19 AAU/mL
Enzyme working range: 0.13-0.19 AAU/mL The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in EP 0140410 B2, which disclosure is hereby included by reference.

Acid Alpha-amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, EC 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

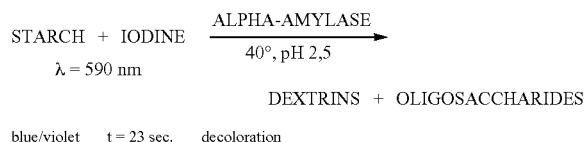

Standard Conditions/Reaction Conditions:
Substrate: Soluble starch, approx. 0.17 g/L
Buffer: Citrate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL A folder EB-SM-0259.02/01 describing this analytical method in more detail is available upon request to Novozymes NS, Denmark, which folder is hereby included by reference.

Example 1

Simultaneous Saccharification and Fermentation (SSF) with *Gloeophyllum sepiarium* AMG The SSF performance of *Gloeophyllum* sp. glucoamylases was tested at different enzyme doses. Fermentation was run under the following conditions:

Substrate: Ground corn was slurried with backset and adjusted its dry substance to approximately 32% (w/w). It was then liquefied at 85° C. and pH 5.8. The liquefied mash had a DE of 13.4.
Temperature: 32° C.
Initial pH: 5.0
Enzyme dose: *Gloeophyllum* sp. AMG produced in *Aspergillus niger* at 30, 40, 55 and 70 micrograms enzyme protein/g DS. Enzymes were compared to a purified sample of the commercial *Talaromyces emersonii* AMG dosed at same dosages. The highest dose of *Talaromyces emersonii* AMG is equivalent to an industry relevant amount of 0.56 AGU/g DS. A control for maximum obtainable saccharification was prepared using excess amounts of commercial AMG and alpha-amylase.
Fermentation To the substrate for SSF, 1000 ppm urea as nitrogen source and 3 ppm penicillin for bacterial control were added; the pH was adjusted to 5.0 with $H_2SO_4$. Aliquots of 5 g mash were transferred to 15 ml centrifuge tubes with a hole drilled at the top for $CO_2$ release. Enzymes and yeast were added and the tubes were placed in a water bath without stirring at 32° C. for 54 hrs. Samples were analyzed in HPLC for determination of ethanol produced during fermentation. The results are shown in the tables below.

TABLE 1

Ethanol g/L produced during SSF with *Gloeophyllum sepiarium* AMG at 30, 40, 55 and 70 micrograms enzyme protein/g DS as compared to *Talaromyces emersonii* AMG.
Control resulted in 133.08 g/L ethanol

| | Enzyme dose (micrograms enzymes protein/g DS) | | | |
|---|---|---|---|---|
| | 30 | 40 | 55 | 70 |
| *Talaromyces emersonii* (SEQ ID NO: 20) | 110.3 | 119.8 | 124.9 | 126.9 |
| *Gloeophyllum sepiarium* (SEQ ID NO: 2) | 115.5 | 122.6 | 130.8 | 130.7 |

TABLE 2

Ethanol g/L produced during SSF with *Gloeophyllum sepiarium* AMG at 30, 40, 55 and 70 micrograms enzyme protein/g DS as compared to *Talaromyces emersonii* AMG.
Control resulted in 131.9 g/L ethanol

| | Enzyme dose (micrograms enzyme protein/g DS) | | | |
|---|---|---|---|---|
| | 30 | 40 | 55 | 70 |
| *Talaromyces emersonii* (SEQ ID NO: 20) | 110.4 | 118.9 | 123.4 | 125.6 |
| *Gloeophyllum sepiarium* (SEQ ID NO: 4) | 113.0 | 121.1 | 129.0 | 129.5 |

TABLE 3

Ethanol yield produced during SSF with *Gloeophyllum* sp. AMG at 30, 40, 55 and 70 micrograms enzyme protein/g DS as compared to *Talaromyces emersonii* AMG and *Trametes cingulata* AMG.
Control resulted in 100% yield.

| | Enzyme dose (micrograms enzyme protein/g DS) | | | |
|---|---|---|---|---|
| | 30 | 40 | 55 | 70 |
| *Gloeophyllum sepiarium* (SEQ ID NO: 2) | 87% | 92% | 98% | 98% |
| *Gloeophyllum trabeum* (SEQ ID NO: 6) | 93% | 97% | 97% | 98% |
| *Gloeophyllum trabeum* (SEQ ID NO: 14) | 88% | 97% | 97% | 98% |
| *Trametes cingulata* AMG G1 (SEQ ID NO: 22) | 87% | 90% | 97% | 98% |
| *Talaromyces emersonii*, T-AMG (SEQ ID NO: 20) | 83% | 90% | 94% | 95% |

Example 2

Specific Activity of *Gloeophyllum* sp. AMGs Compared to *Trametes cingulata* AMG Specific activity was calculated by dividing the glucoamylase AGU-activity (according to the procedure described above) and enzyme protein from each preparation (AA analysis). The table below shows the results for the different *Gloeophyllum* sp. AMGs compared to the *Trametes cingulata* AMG.

| Specific activity | [AGU/mg] |
| --- | --- |
| *Trametes cingulata* AMG G1, SEQ ID NO: 22 | 5.6 |
| *Gloeophyllum sepiarium* AMG, SEQ ID NO: 4 | 6.3 |
| *Gloeophyllum sepiarium* AMG, SEQ ID NO: 2 | 7.2 |
| *Gloeophyllum trabeum*, SEQ ID NO: 16 | 6.1 |
| *Gloeophyllum trabeum*, SEQ ID NO: 18 | 6.0 |
| *Gloeophyllum trabeum*, SEQ ID NO: 14 | 7.2 |
| *Gloeophyllum trabeum*, SEQ ID NO: 6 | 6.5 |

Deposit of Biological Material

The following biological material has been deposited under the terms of the Budapest Treaty with Deutsche Sammlung von Mikroorganismen and Zellkulturen GmbH (DSM), Mascheroder Weg 1 B, D-38124 Braunschweig, Germany, and given the following accession number:

Deposit: *E. coli* strain NN059223 with plasmid comprising sequence D7279 (SEQ ID NO: 1)

Accession Number: DSM 23222 Date of Deposit: Jan. 13, 2010

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The invention claimed is:

1. A method of producing a polypeptide having glucoamylase activity, having at least 95% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, comprising:
   (a) cultivating a host cell transformed with a nucleic acid construct comprising a nucleotide sequence encoding the polypeptide under conditions conducive for production of the polypeptide; and
   (b) recovering the polypeptide.

2. The process of claim 1, wherein the polypeptide has at least 97% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

3. The process of claim 1, wherein the polypeptide comprises SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

4. A method of producing the polypeptide having glucoamylase activity, having a catalytic domain that has at least 95% sequence identity to the sequence of amino acids 19 to 474 of SEQ ID NO: 2, SEQ ID NO: 4, SEQ ID NO: 6, SEQ ID NO: 8, SEQ ID NO: 10, SEQ ID NO: 12, SEQ ID NO: 14 or amino acids 19 to 471 of SEQ ID NO: 16 or SEQ ID NO: 18, comprising:
   (a) cultivating a host cell transformed with a nucleic acid construct comprising a nucleotide sequence encoding the polypeptide under conditions conducive for production of the polypeptide; and
   (b) recovering the polypeptide.

5. The process of claim 4, wherein the polypeptide has at least 95% sequence identity to the sequence of amino acids 18 to 573 of SEQ ID NO: 2, SEQ ID NO: 4, SEQ ID NO: 6, SEQ ID NO: 8, SEQ ID NO: 10, SEQ ID NO: 12, SEQ ID NO: 14, or amino adds 18 to 576 of SEQ ID NO: 16, or SEQ ID NO: 18.

6. The process of claim 4, wherein the polypeptide has at least 97% sequence identity to the sequence of amino acids 18 to 573 of SEQ ID NO: 2, SEQ ID NO: 4, SEQ ID NO: 6, SEQ ID NO: 8, SEQ ID NO: 10, SEQ ID NO: 12, SEQ ID NO: 14, or amino acids 18 to 576 of SEQ ID NO: 16, or SEQ ID NO: 18.

* * * * *